United States Patent
McClurken et al.

(10) Patent No.: US 7,815,634 B2
(45) Date of Patent: Oct. 19, 2010

(54) FLUID DELIVERY SYSTEM AND CONTROLLER FOR ELECTROSURGICAL DEVICES

(75) Inventors: Michael E. McClurken, Durham, NH (US); Robert Luzzi, Exeter, NH (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 258 days.

(21) Appl. No.: 10/746,222

(22) Filed: Dec. 22, 2003

(65) Prior Publication Data

US 2004/0138655 A1 Jul. 15, 2004

Related U.S. Application Data

(63) Continuation of application No. 09/797,049, filed on Mar. 1, 2001, now Pat. No. 6,702,810.

(60) Provisional application No. 60/187,114, filed on Mar. 6, 2000.

(51) Int. Cl.
*A61B 18/10* (2006.01)
(52) U.S. Cl. .............................. 606/34; 607/105; 606/41
(58) Field of Classification Search ............. 606/27–34, 606/41, 42; 607/101–105
See application file for complete search history.

(56) References Cited

U.S. PATENT DOCUMENTS

| | | | |
|---|---|---|---|
| 623,022 A | 4/1899 | Johnson | |
| 1,735,271 A | 11/1929 | Groff | |
| 1,814,791 A | 7/1931 | Ende | |
| 2,002,594 A | 5/1935 | Wappler et al. | |
| 2,031,682 A | 2/1936 | Wappler et al. | |
| 2,102,270 A | 12/1937 | Hyams | |
| 2,275,167 A | 3/1942 | Bierman | |
| 2,888,928 A | 6/1959 | Seiger | |
| 3,163,166 A | 12/1964 | Brent et al. | |
| 3,682,130 A | 8/1972 | Jeffers | |
| 3,750,650 A | 8/1973 | Ruttgers | |
| 3,901,241 A | 8/1975 | Allen, Jr. | |
| 4,037,590 A | 7/1977 | Dohring et al. | |

(Continued)

FOREIGN PATENT DOCUMENTS

DE 1 007 960 5/1957

(Continued)

OTHER PUBLICATIONS

Beer, Edwin, "Removal of Neoplasms of the Urinary Bladder", JAMA., Sep. 9, 1983; 250(10): pp. 1324-1325.

(Continued)

*Primary Examiner*—Michael Peffley
(74) *Attorney, Agent, or Firm*—Grossman, Tucker, Perreault & Pfleger, PLLC

(57) ABSTRACT

The invention provides a system for treating tissue that includes a power measurement device, a flow rate controller coupled to the power measurement device, and an electrosurgical device configured and arranged to provide radio frequency power and conductive fluid to the tissue, wherein the flow rate controller is configured and arranged to modify a flow rate of the conductive fluid to the tissue, based on signals from the power measurement device. The invention also provides methods and devices for modifying flow rate of conductive fluid to tissue based on measurement of radio frequency power delivered to the tissue.

7 Claims, 11 Drawing Sheets

U.S. PATENT DOCUMENTS

| | | |
|---|---|---|
| 4,060,088 A | 11/1977 | Morrison, Jr. et al. |
| 4,116,198 A | 9/1978 | Roos |
| 4,244,371 A | 1/1981 | Farin |
| 4,276,874 A | 7/1981 | Wolvek et al. |
| 4,301,802 A | 11/1981 | Poler |
| 4,307,720 A | 12/1981 | Weber, Jr. |
| 4,321,931 A | 3/1982 | Hon |
| 4,326,529 A | 4/1982 | Doss et al. |
| 4,342,218 A | 8/1982 | Fox |
| 4,355,642 A | 10/1982 | Alferness |
| 4,381,007 A | 4/1983 | Doss |
| 4,532,924 A | 8/1985 | Auth et al. |
| 4,567,890 A | 2/1986 | Ohta et al. |
| 4,602,628 A | 7/1986 | Allen, Jr. |
| 4,671,274 A | 6/1987 | Sorochenko |
| 4,674,499 A | 6/1987 | Pao |
| 4,919,129 A | 4/1990 | Weber, Jr. |
| 4,920,982 A | 5/1990 | Goldstein |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,976,711 A | 12/1990 | Parins et al. |
| 4,985,030 A | 1/1991 | Melzer et al. |
| 4,998,933 A | 3/1991 | Eggers et al. |
| 5,009,656 A | 4/1991 | Reimels |
| 5,013,312 A | 5/1991 | Parins et al. |
| 5,035,696 A | 7/1991 | Rydell |
| 5,071,419 A | 12/1991 | Rydell et al. |
| 5,080,660 A | 1/1992 | Buelna |
| 5,122,138 A | 6/1992 | Manwaring |
| 5,125,928 A | 6/1992 | Parins et al. |
| 5,147,357 A | 9/1992 | Rose et al. |
| 5,151,102 A | 9/1992 | Kamiyama et al. |
| 5,156,613 A | 10/1992 | Sawyer |
| 5,167,659 A | 12/1992 | Ohtomo et al. |
| 5,171,311 A | 12/1992 | Rydell et al. |
| 5,190,541 A | 3/1993 | Abele et al. |
| 5,195,959 A | 3/1993 | Smith |
| 5,197,963 A | 3/1993 | Parins |
| 5,197,964 A | 3/1993 | Parins |
| 5,217,460 A | 6/1993 | Knoepfler |
| 5,234,428 A | 8/1993 | Kaufman |
| 5,242,441 A | 9/1993 | Avitall |
| 5,242,442 A | 9/1993 | Hirschfeld |
| 5,254,117 A | 10/1993 | Rigby |
| 5,269,780 A | 12/1993 | Roos |
| 5,269,781 A | 12/1993 | Hewell, III |
| 5,277,696 A | 1/1994 | Hagen |
| 5,281,215 A | 1/1994 | Milder |
| 5,281,216 A | 1/1994 | Klicek |
| 5,282,799 A | 2/1994 | Rydell |
| 5,290,286 A | 3/1994 | Parins |
| 5,300,087 A | 4/1994 | Knoepfler |
| 5,313,943 A | 5/1994 | Houser et al. |
| 5,318,589 A | 6/1994 | Lichtman |
| 5,322,503 A | 6/1994 | Desai |
| 5,330,521 A | 7/1994 | Cohen |
| 5,334,193 A | 8/1994 | Nardella |
| 5,336,220 A | 8/1994 | Ryan |
| 5,342,357 A | 8/1994 | Nardella |
| 5,342,359 A | 8/1994 | Rydell |
| 5,348,554 A | 9/1994 | Imran et al. |
| 5,364,394 A | 11/1994 | Mehl |
| 5,383,874 A | 1/1995 | Jackson et al. |
| 5,383,876 A | 1/1995 | Nardella |
| 5,395,312 A | 3/1995 | Desai |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,344 A | 4/1995 | Williamson et al. |
| 5,405,376 A | 4/1995 | Mulier et al. |
| 5,417,672 A | 5/1995 | Nita et al. |
| 5,417,709 A | 5/1995 | Slater |
| 5,431,168 A | 7/1995 | Webster et al. |
| 5,431,649 A | 7/1995 | Mulier et al. |
| 5,433,708 A | 7/1995 | Nichols et al. |
| 5,437,662 A | 8/1995 | Nardella |
| 5,437,664 A | 8/1995 | Cohen et al. |
| 5,441,498 A | 8/1995 | Perkins |
| 5,441,503 A | 8/1995 | Considine et al. |
| 5,445,638 A | 8/1995 | Rydell et al. |
| 5,456,682 A | 10/1995 | Edwards et al. |
| 5,456,684 A | 10/1995 | Schmidt et al. |
| 5,458,596 A | 10/1995 | Lax et al. |
| 5,458,597 A | 10/1995 | Edwards et al. |
| 5,458,598 A | 10/1995 | Feinberg et al. |
| 5,460,629 A | 10/1995 | Shlain et al. |
| 5,462,521 A | 10/1995 | Brucker et al. |
| 5,472,441 A | 12/1995 | Edwards et al. |
| 5,472,443 A | 12/1995 | Cordis et al. |
| 5,487,385 A | 1/1996 | Avitall |
| 5,490,819 A | 2/1996 | Nicholas et al. |
| 5,500,012 A | 3/1996 | Brucker et al. |
| 5,514,130 A | 5/1996 | Baker |
| 5,522,815 A | 6/1996 | Durgin, Jr. et al. |
| 5,536,267 A | 7/1996 | Edwards et al. |
| 5,540,562 A * | 7/1996 | Giter .................. 417/254 |
| 5,542,928 A | 8/1996 | Evans et al. |
| 5,542,945 A | 8/1996 | Fritzsch |
| 5,556,397 A | 9/1996 | Long |
| 5,558,671 A | 9/1996 | Yates |
| 5,562,503 A | 10/1996 | Ellman et al. |
| 5,562,702 A | 10/1996 | Huitema et al. |
| 5,562,703 A | 10/1996 | Desai |
| 5,564,440 A | 10/1996 | Swartz et al. |
| 5,569,242 A | 10/1996 | Lax et al. |
| 5,569,243 A | 10/1996 | Kortenbach et al. |
| 5,573,424 A | 11/1996 | Poppe |
| 5,573,533 A | 11/1996 | Strul |
| 5,575,810 A | 11/1996 | Swanson et al. |
| 5,584,872 A | 12/1996 | LaFontaine et al. |
| 5,599,346 A | 2/1997 | Edwards et al. |
| 5,599,350 A | 2/1997 | Schulze et al. |
| 5,605,539 A | 2/1997 | Buelna et al. |
| 5,609,151 A | 3/1997 | Mulier et al. |
| 5,633,578 A | 5/1997 | Eggers et al. |
| 5,637,110 A | 6/1997 | Pennybacker et al. |
| 5,640,955 A | 6/1997 | Ockuly et al. |
| 5,643,197 A | 7/1997 | Brucker et al. |
| 5,647,869 A | 7/1997 | Goble et al. |
| 5,647,871 A | 7/1997 | Levine et al. |
| 5,653,692 A | 8/1997 | Masterson et al. |
| 5,660,836 A | 8/1997 | Knowlton |
| 5,676,662 A | 10/1997 | Fleischhacker et al. |
| 5,676,693 A | 10/1997 | LaFontaine |
| 5,681,282 A | 10/1997 | Eggers et al. |
| 5,681,294 A | 10/1997 | Osborne et al. |
| 5,683,366 A | 11/1997 | Eggers et al. |
| 5,683,384 A | 11/1997 | Gough et al. |
| 5,687,723 A | 11/1997 | Avitall |
| 5,688,270 A | 11/1997 | Yates et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,702,386 A | 12/1997 | Stern et al. |
| 5,709,680 A | 1/1998 | Yates et al. |
| 5,713,896 A | 2/1998 | Nardella |
| 5,718,241 A | 2/1998 | Ben-Haim et al. |
| 5,718,701 A | 2/1998 | Shai et al. |

| | | | | | |
|---|---|---|---|---|---|
| 5,718,703 A | 2/1998 | Chin | 5,980,516 A | 11/1999 | Mulier et al. |
| 5,722,400 A | 3/1998 | Ockuly et al. | 5,989,248 A | 11/1999 | Tu et al. |
| 5,725,524 A | 3/1998 | Mulier et al. | 5,992,418 A | 11/1999 | de la Rama et al. |
| 5,730,127 A | 3/1998 | Avitall | 5,993,412 A | 11/1999 | Deily et al. |
| 5,735,846 A | 4/1998 | Panescu et al. | 6,003,517 A | 12/1999 | Sheffield et al. |
| 5,743,903 A | 4/1998 | Stern et al. | 6,004,316 A | 12/1999 | Laufer |
| 5,746,739 A | 5/1998 | Sutter | 6,004,319 A | 12/1999 | Goble et al. |
| 5,749,869 A | 5/1998 | Lindenmeier et al. | 6,007,570 A | 12/1999 | Sharkey et al. |
| 5,755,717 A | 5/1998 | Yates et al. | 6,010,500 A | 1/2000 | Sherman et al. |
| 5,755,753 A | 5/1998 | Knowlton | 6,015,391 A | 1/2000 | Rishton et al. |
| 5,766,153 A | 6/1998 | Eggers et al. | 6,015,407 A | 1/2000 | Rieb et al. |
| 5,766,167 A | 6/1998 | Eggers et al. | 6,016,809 A | 1/2000 | Mulier et al. |
| 5,785,705 A | 7/1998 | Baker | 6,017,338 A | 1/2000 | Brucker et al. |
| 5,785,706 A | 7/1998 | Bednarek | 6,018,676 A | 1/2000 | Davis et al. |
| 5,792,140 A | 8/1998 | Tu et al. | 6,019,757 A | 2/2000 | Scheldrup |
| 5,797,905 A | 8/1998 | Fleischman et al. | 6,024,733 A | 2/2000 | Eggers et al. |
| 5,797,960 A | 8/1998 | Stevens et al. | 6,027,501 A | 2/2000 | Goble et al. |
| 5,800,413 A | 9/1998 | Swartz et al. | 6,030,379 A | 2/2000 | Panescu et al. |
| 5,800,482 A | 9/1998 | Pomeranz et al. | 6,030,381 A | 2/2000 | Jones |
| 5,807,393 A | 9/1998 | Williamson et al. | 6,032,077 A | 2/2000 | Pomeranz |
| 5,807,395 A | 9/1998 | Mulier et al. | 6,032,674 A | 3/2000 | Eggers et al. |
| 5,810,764 A | 9/1998 | Eggers et al. | 6,033,398 A | 3/2000 | Farley et al. |
| 5,810,805 A | 9/1998 | Sutcu et al. | 6,035,238 A | 3/2000 | Ingle et al. |
| 5,810,811 A | 9/1998 | Yates et al. | 6,036,687 A | 3/2000 | Laufer et al. |
| 5,817,093 A | 10/1998 | Williamson et al. | 6,045,532 A | 4/2000 | Eggers et al. |
| 5,823,956 A | 10/1998 | Roth et al. | 6,047,700 A | 4/2000 | Eggers et al. |
| 5,827,271 A | 10/1998 | Buysse et al. | 6,048,333 A | 4/2000 | Lennox et al. |
| 5,827,281 A | 10/1998 | Levin | 6,053,172 A | 4/2000 | Hovda et al. |
| 5,833,703 A | 11/1998 | Manushakian | 6,053,912 A | 4/2000 | Panescu et al. |
| 5,843,019 A | 12/1998 | Eggers et al. | 6,056,744 A | 5/2000 | Edwards |
| 5,843,021 A | 12/1998 | Edwards et al. | 6,056,745 A | 5/2000 | Panescu et al. |
| 5,843,078 A | 12/1998 | Sharkey | 6,056,746 A | 5/2000 | Goble |
| 5,843,152 A | 12/1998 | Tu et al. | 6,056,747 A | 5/2000 | Saadat et al. |
| 5,855,614 A | 1/1999 | Stevens et al. | 6,059,781 A | 5/2000 | Yamanashi et al. |
| 5,860,951 A | 1/1999 | Eggers et al. | 6,063,079 A | 5/2000 | Hovda et al. |
| 5,860,974 A | 1/1999 | Abele | 6,063,081 A | 5/2000 | Mulier et al. |
| 5,861,002 A | 1/1999 | Desai | 6,066,134 A | 5/2000 | Eggers et al. |
| 5,861,021 A | 1/1999 | Thome et al. | 6,066,139 A | 5/2000 | Ryan et al. |
| 5,868,739 A | 2/1999 | Lindenmeier et al. | 6,068,627 A | 5/2000 | Orszulak et al. |
| 5,871,469 A | 2/1999 | Eggers et al. | 6,068,653 A | 5/2000 | LaFontaine |
| 5,871,524 A | 2/1999 | Knowlton | 6,071,280 A | 6/2000 | Edwards et al. |
| 5,873,855 A | 2/1999 | Eggers et al. | 6,073,051 A | 6/2000 | Sharkey et al. |
| 5,876,398 A | 3/1999 | Mulier et al. | 6,074,389 A | 6/2000 | Levine et al. |
| 5,879,348 A | 3/1999 | Owens et al. | 6,080,151 A | 6/2000 | Swartz et al. |
| 5,888,198 A | 3/1999 | Eggers et al. | 6,081,749 A | 6/2000 | Ingle et al. |
| 5,891,095 A | 4/1999 | Eggers et al. | 6,083,237 A | 7/2000 | Huitema et al. |
| 5,891,141 A | 4/1999 | Rydell | 6,086,585 A | 7/2000 | Hovda et al. |
| 5,891,142 A | 4/1999 | Eggers et al. | 6,086,586 A | 7/2000 | Hooven |
| 5,893,848 A | 4/1999 | Negus et al. | 6,091,995 A | 7/2000 | Ingle et al. |
| 5,895,355 A | 4/1999 | Schaer | 6,093,186 A | 7/2000 | Goble |
| 5,895,417 A | 4/1999 | Pomeranz et al. | 6,095,149 A | 8/2000 | Sharkey et al. |
| 5,897,553 A | 4/1999 | Mulier et al. | 6,096,037 A | 8/2000 | Mulier et al. |
| 5,902,272 A | 5/1999 | Eggers et al. | 6,099,514 A | 8/2000 | Sharkey et al. |
| 5,902,328 A | 5/1999 | LaFontaine et al. | 6,102,046 A | 8/2000 | Weinstein et al. |
| 5,904,711 A | 5/1999 | Flom et al. | 6,105,581 A | 8/2000 | Eggers et al. |
| 5,906,613 A | 5/1999 | Mulier et al. | 6,109,268 A | 8/2000 | Thapliyal et al. |
| 5,913,854 A | 6/1999 | Maguire et al. | 6,113,596 A | 9/2000 | Hooven et al. |
| 5,913,856 A | 6/1999 | Chia et al. | 6,113,597 A | 9/2000 | Eggers et al. |
| 5,919,191 A | 7/1999 | Lennox et al. | 6,117,109 A | 9/2000 | Eggers et al. |
| 5,919,219 A | 7/1999 | Knowlton | 6,122,549 A | 9/2000 | Sharkey et al. |
| 5,921,982 A | 7/1999 | Lesh et al. | H1904 H | 10/2000 | Yates et al. |
| 5,921,983 A | 7/1999 | Shannon, Jr. | 6,126,682 A | 10/2000 | Sharkey et al. |
| 5,925,045 A | 7/1999 | Reimels et al. | 6,135,999 A | 10/2000 | Fanton et al. |
| 5,935,123 A | 8/1999 | Edwards et al. | 6,141,576 A | 10/2000 | Littmann et al. |
| 5,944,715 A | 8/1999 | Goble | 6,142,992 A | 11/2000 | Cheng et al. |
| 5,948,011 A | 9/1999 | Knowlton | 6,149,620 A | 11/2000 | Baker et al. |
| 5,951,549 A | 9/1999 | Richardson et al. | 6,159,194 A | 12/2000 | Eggers et al. |
| 5,954,716 A | 9/1999 | Sharkey et al. | 6,159,208 A | 12/2000 | Hovda et al. |
| 5,957,919 A | 9/1999 | Laufer | 6,165,169 A | 12/2000 | Panescu et al. |
| 5,964,755 A | 10/1999 | Edwards | 6,165,175 A | 12/2000 | Wampler et al. |
| 5,971,983 A | 10/1999 | Lesh | 6,168,594 B1 | 1/2001 | LaFontaine et al. |
| 5,976,128 A | 11/1999 | Schilling et al. | 6,171,275 B1 | 1/2001 | Webster, Jr. |
| 5,980,504 A | 11/1999 | Sharkey et al. | 6,174,308 B1 | 1/2001 | Goble et al. |

| | | | | | | |
|---|---|---|---|---|---|---|
| 6,174,309 B1 | 1/2001 | Wrublewski et al. | 6,363,937 B1 | 4/2002 | Hovda et al. | |
| 6,176,857 B1 | 1/2001 | Ashley | 6,371,956 B1 | 4/2002 | Wilson et al. | |
| 6,179,824 B1 | 1/2001 | Eggers et al. | 6,379,350 B1 | 4/2002 | Sharkey et al. | |
| 6,179,836 B1 | 1/2001 | Eggers et al. | 6,379,351 B1 | 4/2002 | Thapliyal et al. | |
| 6,183,469 B1 | 2/2001 | Thapliyal et al. | 6,391,025 B1 | 5/2002 | Weinstein et al. | |
| 6,190,381 B1 | 2/2001 | Olsen et al. | 6,391,028 B1 | 5/2002 | Fanton et al. | |
| 6,190,384 B1 | 2/2001 | Ouchi | 6,402,742 B1 | 6/2002 | Blewett et al. | |
| 6,193,715 B1 | 2/2001 | Wrublewski et al. | 6,409,722 B1 * | 6/2002 | Hoey et al. | 606/34 |
| 6,193,716 B1 | 2/2001 | Shannon, Jr. | 6,409,723 B1 | 6/2002 | Edwards | |
| 6,203,542 B1 | 3/2001 | Ellsberry et al. | H2037 H | 7/2002 | Yates et al. | |
| 6,210,402 B1 | 4/2001 | Olsen et al. | 6,416,507 B1 | 7/2002 | Eggers et al. | |
| 6,210,406 B1 | 4/2001 | Webster | 6,416,508 B1 | 7/2002 | Eggers et al. | |
| 6,210,410 B1 | 4/2001 | Farin et al. | 6,416,509 B1 | 7/2002 | Goble et al. | |
| 6,210,411 B1 | 4/2001 | Hofmann et al. | 6,425,877 B1 | 7/2002 | Edwards | |
| 6,212,426 B1 | 4/2001 | Swanson | 6,432,103 B1 | 8/2002 | Ellsberry et al. | |
| 6,216,704 B1 | 4/2001 | Ingle et al. | 6,440,130 B1 | 8/2002 | Mulier et al. | |
| 6,217,576 B1 | 4/2001 | Tu et al. | 6,443,952 B1 | 9/2002 | Mulier et al. | |
| 6,221,039 B1 | 4/2001 | Durgin et al. | 6,451,017 B1 | 9/2002 | Moutafis et al. | |
| 6,221,069 B1 | 4/2001 | Daikuzono | 6,458,123 B1 | 10/2002 | Brucker et al. | |
| 6,224,592 B1 | 5/2001 | Eggers et al. | 6,458,130 B1 | 10/2002 | Frazier et al. | |
| 6,224,593 B1 | 5/2001 | Ryan et al. | 6,461,350 B1 | 10/2002 | Underwood et al. | |
| 6,226,554 B1 | 5/2001 | Tu et al. | 6,461,354 B1 | 10/2002 | Olsen et al. | |
| 6,228,078 B1 | 5/2001 | Eggers et al. | 6,461,357 B1 | 10/2002 | Sharkey et al. | |
| 6,228,082 B1 | 5/2001 | Baker et al. | 6,464,695 B2 | 10/2002 | Hovda et al. | |
| 6,231,591 B1 | 5/2001 | Desai | 6,468,270 B1 | 10/2002 | Hovda et al. | |
| 6,235,020 B1 | 5/2001 | Cheng et al. | 6,468,274 B1 | 10/2002 | Alleyne et al. | |
| 6,236,891 B1 | 5/2001 | Ingle et al. | 6,468,275 B1 | 10/2002 | Wampler et al. | |
| 6,238,387 B1 | 5/2001 | Miller, III | 6,471,698 B1 | 10/2002 | Edwards et al. | |
| 6,238,391 B1 | 5/2001 | Olsen et al. | 6,475,216 B2 | 11/2002 | Mulier et al. | |
| 6,238,393 B1 | 5/2001 | Mulier et al. | 6,478,793 B1 | 11/2002 | Cosman et al. | |
| 6,241,753 B1 | 6/2001 | Knowlton | 6,482,202 B1 | 11/2002 | Goble et al. | |
| 6,241,754 B1 | 6/2001 | Swanson et al. | 6,485,490 B2 | 11/2002 | Wampler et al. | |
| 6,251,110 B1 | 6/2001 | Wampler | 6,488,680 B1 | 12/2002 | Francischelli et al. | |
| 6,254,600 B1 | 7/2001 | Willink et al. | 6,493,589 B1 | 12/2002 | Medhkour et al. | |
| 6,258,086 B1 | 7/2001 | Ashley et al. | 6,494,902 B2 | 12/2002 | Hoey et al. | |
| 6,258,087 B1 * | 7/2001 | Edwards et al. ............... 606/41 | 6,497,704 B2 | 12/2002 | Ein-Gai | |
| 6,261,311 B1 | 7/2001 | Sharkey et al. | 6,497,705 B2 | 12/2002 | Comben | |
| 6,264,650 B1 | 7/2001 | Hovda et al. | 6,506,189 B1 | 1/2003 | Rittman, III et al. | |
| 6,264,651 B1 | 7/2001 | Underwood et al. | 6,508,815 B1 | 1/2003 | Strul et al. | |
| 6,264,652 B1 | 7/2001 | Eggers et al. | 6,517,536 B2 | 2/2003 | Hooven et al. | |
| 6,264,654 B1 | 7/2001 | Swartz et al. | 6,526,320 B2 | 2/2003 | Mitchell | |
| 6,266,551 B1 | 7/2001 | Osadchy et al. | 6,537,248 B2 | 3/2003 | Mulier et al. | |
| 6,277,112 B1 | 8/2001 | Underwood et al. | 6,537,272 B2 | 3/2003 | Christopherson et al. | |
| 6,280,440 B1 | 8/2001 | Gocho | 6,539,265 B2 | 3/2003 | Medhkour et al. | |
| 6,283,961 B1 | 9/2001 | Underwood et al. | 6,558,379 B1 | 5/2003 | Batchelor et al. | |
| 6,283,988 B1 | 9/2001 | Laufer et al. | 6,558,385 B1 | 5/2003 | McClurken et al. | |
| 6,283,989 B1 | 9/2001 | Laufer et al. | 6,575,969 B1 * | 6/2003 | Rittman et al. | 606/41 |
| 6,290,715 B1 | 9/2001 | Sharkey et al. | 6,577,902 B1 | 6/2003 | Laufer et al. | |
| 6,293,942 B1 | 9/2001 | Goble et al. | 6,579,288 B1 | 6/2003 | Swanson et al. | |
| 6,293,945 B1 | 9/2001 | Parins et al. | 6,585,732 B2 | 7/2003 | Mulier et al. | |
| 6,296,636 B1 | 10/2001 | Cheng et al. | 6,602,248 B1 | 8/2003 | Sharps et al. | |
| 6,296,638 B1 | 10/2001 | Davison et al. | 6,603,988 B2 | 8/2003 | Dowlatshahi | |
| 6,296,640 B1 | 10/2001 | Wampler et al. | 6,610,060 B2 | 8/2003 | Mulier et al. | |
| 6,299,633 B1 | 10/2001 | Laufer | 6,613,048 B2 | 9/2003 | Mulier et al. | |
| 6,302,903 B1 | 10/2001 | Mulier et al. | 6,623,515 B2 | 9/2003 | Mulier et al. | |
| 6,306,134 B1 | 10/2001 | Goble et al. | 6,626,899 B2 | 9/2003 | Houser et al. | |
| 6,309,387 B1 | 10/2001 | Eggers et al. | 6,635,034 B1 | 10/2003 | Cosmescu | |
| 6,311,090 B1 | 10/2001 | Knowlton | 6,645,202 B1 | 11/2003 | Pless et al. | |
| 6,312,408 B1 | 11/2001 | Eggers et al. | 6,666,862 B2 * | 12/2003 | Jain et al. | 606/41 |
| 6,312,430 B1 | 11/2001 | Wilson et al. | 6,669,692 B1 | 12/2003 | Nelson et al. | |
| 6,315,777 B1 | 11/2001 | Comben | 6,676,660 B2 | 1/2004 | Wampler | |
| 6,322,549 B1 | 11/2001 | Eggers et al. | 6,679,882 B1 | 1/2004 | Kornerup | |
| 6,322,559 B1 | 11/2001 | Daulton et al. | 6,682,501 B1 | 1/2004 | Nelson et al. | |
| 6,327,505 B1 | 12/2001 | Medhkour et al. | 6,682,527 B2 | 1/2004 | Strul | |
| 6,328,735 B1 | 12/2001 | Curley et al. | 6,682,528 B2 | 1/2004 | Frazier et al. | |
| 6,328,736 B1 | 12/2001 | Mulier et al. | 6,685,700 B2 | 2/2004 | Behl et al. | |
| 6,336,926 B1 | 1/2002 | Goble | 6,685,701 B2 | 2/2004 | Orszulak et al. | |
| 6,350,262 B1 | 2/2002 | Ashley | 6,685,704 B2 | 2/2004 | Greep | |
| 6,350,276 B1 | 2/2002 | Knowlton | 6,689,129 B2 | 2/2004 | Baker | |
| 6,352,533 B1 | 3/2002 | Ellman et al. | 6,689,131 B2 | 2/2004 | McClurken | |
| 6,355,032 B1 | 3/2002 | Hovda et al. | 6,692,489 B1 | 2/2004 | Heim et al. | |
| 6,358,245 B1 | 3/2002 | Edwards et al. | 6,694,984 B2 | 2/2004 | Habib | |
| 6,358,248 B1 | 3/2002 | Mulier et al. | 6,695,837 B2 | 2/2004 | Howell | |

| Patent | Kind | Date | Inventor |
|---|---|---|---|
| 6,695,840 | B2 | 2/2004 | Schulze |
| 6,699,240 | B2 | 3/2004 | Francischelli |
| 6,699,242 | B2 | 3/2004 | Heggeness |
| 6,699,244 | B2 | 3/2004 | Carranza et al. |
| 6,699,268 | B2 | 3/2004 | Kordis et al. |
| 6,702,810 | B2 | 3/2004 | McClurken et al. |
| 6,702,812 | B2 | 3/2004 | Cosmescu |
| 6,706,039 | B2 | 3/2004 | Mulier et al. |
| 6,712,074 | B2 | 3/2004 | Edwards et al. |
| 6,712,811 | B2 | 3/2004 | Underwood et al. |
| 6,712,813 | B2 | 3/2004 | Ellman et al. |
| 6,712,816 | B2 | 3/2004 | Hung et al. |
| 6,716,211 | B2 | 4/2004 | Mulier et al. |
| 6,719,754 | B2 | 4/2004 | Underwood et al. |
| 6,723,094 | B1 | 4/2004 | Desinger |
| 6,726,683 | B1 | 4/2004 | Shaw |
| 6,726,684 | B1 | 4/2004 | Woloszko et al. |
| 6,726,686 | B2 | 4/2004 | Buysse et al. |
| 6,730,081 | B1 | 5/2004 | Desai |
| 6,733,496 | B2 | 5/2004 | Sharkey et al. |
| 6,733,498 | B2 | 5/2004 | Paton et al. |
| 6,733,501 | B2 | 5/2004 | Levine |
| 6,736,810 | B2 | 5/2004 | Hoey et al. |
| 6,740,058 | B2 | 5/2004 | Lal et al. |
| 6,740,079 | B1 | 5/2004 | Eggers et al. |
| 6,740,082 | B2 | 5/2004 | Shadduck |
| 6,740,084 | B2 | 5/2004 | Ryan |
| 6,740,102 | B2 | 5/2004 | Hess et al. |
| 6,743,197 | B1 | 6/2004 | Edwards |
| 6,743,229 | B2 | 6/2004 | Buysse et al. |
| 6,743,230 | B2 | 6/2004 | Lutze et al. |
| 6,746,447 | B2 | 6/2004 | Davison et al. |
| 6,755,825 | B2 | 6/2004 | Shoenman et al. |
| 6,755,827 | B2 | 6/2004 | Mulier et al. |
| 6,757,565 | B2 | 6/2004 | Sharkey et al. |
| 6,758,846 | B2 | 7/2004 | Goble et al. |
| 6,761,718 | B2 | 7/2004 | Madsen |
| 6,764,487 | B2 | 7/2004 | Mulier et al. |
| 6,766,202 | B2 | 7/2004 | Underwood et al. |
| 6,766,817 | B2 | 7/2004 | Da Silva |
| 6,770,070 | B1 | 8/2004 | Balbierz |
| 6,770,071 | B2 | 8/2004 | Woloszko et al. |
| 6,770,072 | B1 | 8/2004 | Truckai et al. |
| 6,772,012 | B2 | 8/2004 | Ricart et al. |
| 6,772,013 | B1 | 8/2004 | Ingle et al. |
| 6,775,575 | B2 | 8/2004 | Bommannan et al. |
| 6,776,780 | B2 | 8/2004 | Mulier et al. |
| 6,780,177 | B2 | 8/2004 | Shafirstein et al. |
| 6,780,180 | B1 | 8/2004 | Goble et al. |
| 6,786,906 | B1 | 9/2004 | Cobb |
| 6,796,981 | B2 | 9/2004 | Wham et al. |
| 6,800,077 | B1 | 10/2004 | Mucko et al. |
| 6,802,842 | B2 | 10/2004 | Ellman et al. |
| 6,802,843 | B2 | 10/2004 | Truckai et al. |
| 6,808,525 | B2 | 10/2004 | Latterell et al. |
| 6,813,520 | B2 | 11/2004 | Truckai et al. |
| 6,814,714 | B1 | 11/2004 | Novak et al. |
| 6,814,731 | B2 | 11/2004 | Swanson |
| 6,821,273 | B2 | 11/2004 | Mollenauer |
| 6,827,713 | B2 | 12/2004 | Bek et al. |
| 6,827,725 | B2 | 12/2004 | Batchelor et al. |
| 6,832,996 | B2 | 12/2004 | Woloszko |
| 6,832,997 | B2 | 12/2004 | Uchida et al. |
| 6,835,195 | B2 | 12/2004 | Schulze et al. |
| 6,836,688 | B2 | 12/2004 | Ingle et al. |
| 6,843,789 | B2 | 1/2005 | Goble |
| 6,845,264 | B1 | 1/2005 | Skladnev et al. |
| 6,849,073 | B2 | 2/2005 | Hoey et al. |
| 6,855,145 | B2 | 2/2005 | Ciarrocca |
| 6,858,028 | B2 | 2/2005 | Mulier et al. |
| 6,860,882 | B2 | 3/2005 | Battles et al. |
| 6,863,669 | B2 | 3/2005 | Spitzer |
| 6,864,686 | B2 | 3/2005 | Novak et al. |
| 6,881,214 | B2 | 4/2005 | Cosman et al. |
| 6,882,885 | B2 | 4/2005 | Levy, Jr. et al. |
| 6,887,237 | B2 | 5/2005 | McGaffigan |
| 6,887,240 | B1 | 5/2005 | Lands et al. |
| 6,893,435 | B2 | 5/2005 | Goble |
| 6,893,440 | B2 | 5/2005 | Durgin et al. |
| 6,896,672 | B1 | 5/2005 | Eggers et al. |
| 6,896,674 | B1 | 5/2005 | Woloszko et al. |
| 6,899,712 | B2 | 5/2005 | Moutafis et al. |
| 6,905,497 | B2 | 6/2005 | Truckai et al. |
| 6,905,499 | B1 | 6/2005 | Mucko et al. |
| 6,911,019 | B2 | 6/2005 | Mulier et al. |
| 6,915,806 | B2 | 7/2005 | Pacek et al. |
| 6,918,404 | B2 | 7/2005 | Da Silva |
| 6,921,398 | B2 | 7/2005 | Carmel et al. |
| 6,921,399 | B2 | 7/2005 | Carmel et al. |
| 6,923,803 | B2 | 8/2005 | Goble |
| 6,923,805 | B1 | 8/2005 | LaFontaine et al. |
| 6,926,706 | B1 | 8/2005 | Sealfon |
| 6,926,716 | B2 | 8/2005 | Baker et al. |
| 6,926,717 | B1 | 8/2005 | Garito et al. |
| 6,929,640 | B1 | 8/2005 | Underwood et al. |
| 6,929,641 | B2 | 8/2005 | Goble et al. |
| 6,929,642 | B2 | 8/2005 | Xiao et al. |
| 6,929,644 | B2 | 8/2005 | Truckai et al. |
| 6,929,645 | B2 | 8/2005 | Battles et al. |
| 6,932,810 | B2 | 8/2005 | Ryan |
| 6,932,815 | B2 | 8/2005 | Sutter |
| 6,942,661 | B2 | 9/2005 | Swanson |
| 6,949,096 | B2 | 9/2005 | Davison et al. |
| 6,949,098 | B2 | 9/2005 | Mulier et al. |
| 6,951,559 | B1 | 10/2005 | Greep |
| 6,953,461 | B2 | 10/2005 | McClurken et al. |
| 6,960,204 | B2 | 11/2005 | Eggers et al. |
| 6,960,207 | B2 | 11/2005 | Vanney et al. |
| 6,960,210 | B2 | 11/2005 | Lands et al. |
| 6,962,589 | B2 | 11/2005 | Mulier et al. |
| 6,964,274 | B1 | 11/2005 | Ryan et al. |
| 6,964,661 | B2 | 11/2005 | Rioux et al. |
| 6,966,907 | B2 | 11/2005 | Goble |
| 6,966,909 | B2 | 11/2005 | Marshall et al. |
| 6,971,394 | B2 | 12/2005 | Sliwa, Jr. et al. |
| 6,974,452 | B1 | 12/2005 | Gille et al. |
| 6,974,453 | B2 | 12/2005 | Woloszko et al. |
| 6,979,332 | B2 | 12/2005 | Adams |
| 6,984,231 | B2 | 1/2006 | Goble et al. |
| 6,986,769 | B2 | 1/2006 | Nelson et al. |
| 6,991,631 | B2 | 1/2006 | Woloszko et al. |
| 7,001,380 | B2 | 2/2006 | Goble |
| 7,001,382 | B2 | 2/2006 | Gallo, Sr. |
| 7,004,941 | B2 | 2/2006 | Tvinnereim et al. |
| 7,004,942 | B2 | 2/2006 | Laird et al. |
| 7,008,419 | B2 | 3/2006 | Shadduck |
| 7,008,421 | B2 | 3/2006 | Daniel et al. |
| 7,033,348 | B2 | 4/2006 | Alfano et al. |
| 7,033,356 | B2 | 4/2006 | Latterell et al. |
| 7,041,096 | B2 | 5/2006 | Malis et al. |
| 7,041,101 | B2 | 5/2006 | Eggers |
| 7,041,102 | B2 | 5/2006 | Truckai et al. |
| 7,052,494 | B2 | 5/2006 | Goble et al. |
| 7,060,064 | B2 | 6/2006 | Allen et al. |
| 7,063,670 | B2 | 6/2006 | Sampson et al. |
| 7,066,586 | B2 | 6/2006 | Da Silva |
| 7,066,932 | B1 | 6/2006 | Morgan et al. |
| 7,066,936 | B2 | 6/2006 | Ryan |
| 7,070,596 | B1 | 7/2006 | Woloszko et al. |
| 7,070,604 | B1 | 7/2006 | Garito et al. |
| 7,074,217 | B2 | 7/2006 | Strul et al. |
| 7,074,219 | B2 | 7/2006 | Levine et al. |
| 7,083,601 | B1 | 8/2006 | Cosmescu |
| 7,087,051 | B2 | 8/2006 | Bourne et al. |
| 7,087,053 | B2 | 8/2006 | Vanney |
| 7,094,215 | B2 | 8/2006 | Davison et al. |

| Patent/Pub No. | Date | Inventor |
|---|---|---|
| 7,101,387 B2 | 9/2006 | Garabedian et al. |
| 7,104,986 B2 | 9/2006 | Hovda et al. |
| 7,112,199 B2 | 9/2006 | Cosmescu |
| 7,115,139 B2 | 10/2006 | McClurken et al. |
| 7,125,406 B2 | 10/2006 | Given |
| 7,147,634 B2 | 12/2006 | Nesbitt |
| 7,147,635 B2 | 12/2006 | Ciarrocca |
| 7,147,637 B2 | 12/2006 | Goble |
| 7,147,638 B2 | 12/2006 | Chapman et al. |
| 7,150,746 B2 | 12/2006 | DeCesare et al. |
| 7,150,747 B1 | 12/2006 | McDonald et al. |
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |
| 2002/0156511 A1 | 10/2002 | Habib |
| 2002/0161364 A1 | 10/2002 | Mulier et al. |
| 2002/0169446 A1 | 11/2002 | Mulier et al. |
| 2002/0177846 A1 | 11/2002 | Mulier et al. |
| 2002/0183733 A1 | 12/2002 | Mulier et al. |
| 2002/0188284 A1 | 12/2002 | To et al. |
| 2002/0193851 A1 | 12/2002 | Silverman et al. |
| 2002/0198524 A1 | 12/2002 | Mulier et al. |
| 2003/0014050 A1 | 1/2003 | Sharkey et al. |
| 2003/0032954 A1 | 2/2003 | Carranza et al. |
| 2003/0032955 A1 | 2/2003 | Mulier et al. |
| 2003/0073989 A1 | 4/2003 | Hoey et al. |
| 2003/0073993 A1 | 4/2003 | Ciarrocca |
| 2003/0114850 A1 | 6/2003 | McClurken et al. |
| 2003/0181902 A1 | 9/2003 | Mulier et al. |
| 2003/0204185 A1 | 10/2003 | Sherman et al. |
| 2003/0216733 A1 | 11/2003 | McClurken et al. |
| 2004/0015162 A1 | 1/2004 | McGaffigan |
| 2004/0015163 A1 | 1/2004 | Buysse et al. |
| 2004/0015215 A1 | 1/2004 | Fredricks et al. |
| 2004/0015216 A1 | 1/2004 | DeSisto |
| 2004/0015218 A1 | 1/2004 | Finch et al. |
| 2004/0019350 A1 | 1/2004 | O'Brien et al. |
| 2004/0024395 A1 | 2/2004 | Ellman et al. |
| 2004/0024396 A1 | 2/2004 | Eggers |
| 2004/0024398 A1 | 2/2004 | Hovda et al. |
| 2004/0024399 A1 | 2/2004 | Sharps et al. |
| 2004/0030327 A1 | 2/2004 | Golan |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030333 A1 | 2/2004 | Goble |
| 2004/0034340 A1 | 2/2004 | Biscup |
| 2004/0034346 A1 | 2/2004 | Stern et al. |
| 2004/0034349 A1 | 2/2004 | Kirwan, Jr. et al. |
| 2004/0034400 A1 | 2/2004 | Ingle et al. |
| 2004/0039429 A1 | 2/2004 | Daniel et al. |
| 2004/0044341 A1 | 3/2004 | Truckai et al. |
| 2004/0054363 A1 | 3/2004 | Vaska et al. |
| 2004/0054365 A1 | 3/2004 | Goble |
| 2004/0054366 A1 | 3/2004 | Davison et al. |
| 2004/0054369 A1 | 3/2004 | Nelson et al. |
| 2004/0054370 A1 | 3/2004 | Given |
| 2004/0059328 A1 | 3/2004 | Daniel et al. |
| 2004/0059363 A1 | 3/2004 | Alvarez et al. |
| 2004/0064023 A1 | 4/2004 | Ryan et al. |
| 2004/0064137 A1 | 4/2004 | Pellegrino et al. |
| 2004/0068306 A1 | 4/2004 | Shadduck |
| 2004/0068307 A1 | 4/2004 | Goble |
| 2004/0073205 A1 | 4/2004 | Treat et al. |
| 2004/0073208 A1 | 4/2004 | Sutter |
| 2004/0078034 A1 | 4/2004 | Acker et al. |
| 2004/0078037 A1 | 4/2004 | Batchelor et al. |
| 2004/0078038 A1 | 4/2004 | Desinger et al. |
| 2004/0082946 A1 | 4/2004 | Malis et al. |
| 2004/0082952 A1 | 4/2004 | Dycus et al. |
| 2004/0087937 A1 | 5/2004 | Eggers et al. |
| 2004/0087939 A1 | 5/2004 | Eggers et al. |
| 2004/0087940 A1 | 5/2004 | Jahns et al. |
| 2004/0087943 A1 | 5/2004 | Dycus et al. |
| 2004/0088029 A1 | 5/2004 | Yamamoto |
| 2004/0092925 A1 | 5/2004 | Rizoiu et al. |
| 2004/0092926 A1 | 5/2004 | Hoey et al. |
| 2004/0097919 A1 | 5/2004 | Wellman et al. |
| 2004/0102770 A1 | 5/2004 | Goble |
| 2004/0102824 A1 | 5/2004 | Sharkey et al. |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0122420 A1 | 6/2004 | Amoah |
| 2004/0122423 A1 | 6/2004 | Dycus et al. |
| 2004/0122494 A1 | 6/2004 | Eggers et al. |
| 2004/0138654 A1 | 7/2004 | Goble |
| 2004/0138655 A1 | 7/2004 | McClurken et al. |
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |

| | | |
|---|---|---|
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |
| 2004/0186535 A1 | 9/2004 | Knowlton |
| 2004/0193148 A1 | 9/2004 | Wham et al. |
| 2004/0193150 A1 | 9/2004 | Sharkey et al. |
| 2004/0193152 A1 | 9/2004 | Sutton et al. |
| 2004/0193211 A1 | 9/2004 | Voegele et al. |
| 2004/0199156 A1 | 10/2004 | Rioux et al. |
| 2004/0199160 A1 | 10/2004 | Slater |
| 2004/0206365 A1 | 10/2004 | Knowlton |
| 2004/0210213 A1 | 10/2004 | Fuimaono et al. |
| 2004/0210214 A1 | 10/2004 | Knowlton |
| 2004/0215181 A1 | 10/2004 | Christopherson et al. |
| 2004/0215182 A1 | 10/2004 | Lee |
| 2004/0215183 A1 | 10/2004 | Hoey et al. |
| 2004/0215184 A1 | 10/2004 | Eggers et al. |
| 2004/0215185 A1 | 10/2004 | Truckai et al. |
| 2004/0215188 A1 | 10/2004 | Mulier et al. |
| 2004/0215235 A1 | 10/2004 | Jackson et al. |
| 2004/0215296 A1 | 10/2004 | Ganz et al. |
| 2004/0220561 A1 | 11/2004 | Kirwan, Jr. et al. |
| 2004/0220562 A1 | 11/2004 | Garabedian et al. |
| 2004/0225288 A1 | 11/2004 | Buysse et al. |
| 2004/0230190 A1 | 11/2004 | Dahla et al. |
| 2004/0236322 A1 | 11/2004 | Mulier et al. |
| 2004/0236324 A1 | 11/2004 | Muller et al. |
| 2004/0243125 A1 | 12/2004 | Dycus et al. |
| 2004/0243163 A1 | 12/2004 | Casiano et al. |
| 2004/0249371 A1 | 12/2004 | Dycus et al. |
| 2004/0249374 A1 | 12/2004 | Tetzlaff et al. |
| 2004/0249425 A1 | 12/2004 | Roy et al. |
| 2004/0260279 A1 | 12/2004 | Goble et al. |
| 2004/0260280 A1 | 12/2004 | Sartor |
| 2004/0260368 A1 | 12/2004 | Ingle et al. |
| 2005/0010205 A1 | 1/2005 | Hovda et al. |
| 2005/0010212 A1 | 1/2005 | McClurken et al. |
| 2005/0015085 A1 | 1/2005 | McClurken et al. |
| 2005/0015086 A1 | 1/2005 | Platt |
| 2005/0015130 A1 | 1/2005 | Gill |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0033292 A1 | 2/2005 | Teitelbaum et al. |
| 2005/0038471 A1 | 2/2005 | Chan et al. |
| 2005/0043728 A1 | 2/2005 | Ciarrocca |
| 2005/0049583 A1 | 3/2005 | Swanson |
| 2005/0049586 A1 | 3/2005 | Daniel et al. |
| 2005/0055019 A1 | 3/2005 | Skarda |
| 2005/0055020 A1 | 3/2005 | Skarda |
| 2005/0059966 A1 | 3/2005 | McClurken et al. |
| 2005/0070888 A1 | 3/2005 | Dimatteo et al. |
| 2005/0070891 A1 | 3/2005 | DeSisto |
| 2005/0070894 A1 | 3/2005 | McClurken |
| 2005/0070896 A1 | 3/2005 | Daniel et al. |
| 2005/0080410 A1 | 4/2005 | Rioux et al. |
| 2005/0080413 A1 | 4/2005 | Canady |
| 2005/0085804 A1 | 4/2005 | McGaffigan |
| 2005/0085809 A1 | 4/2005 | Mucko et al. |
| 2005/0085880 A1 | 4/2005 | Truckai et al. |
| 2005/0090816 A1 | 4/2005 | McClurken et al. |
| 2005/0090819 A1 | 4/2005 | Goble |
| 2005/0096649 A1 | 5/2005 | Adams |
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | WeitKamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |

| | | |
|---|---|---|
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0071270 A1 | 3/2008 | Baker et al. |

FOREIGN PATENT DOCUMENTS

| | | |
|---|---|---|
| EP | 0 175 595 | 3/1986 |
| EP | 0 895 756 A1 | 2/1999 |
| EP | 1 095 627 A1 | 5/2001 |
| EP | 1 157 666 A1 | 11/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 90/03152 | 4/1990 |
| WO | WO 94/02077 A2 | 2/1994 |
| WO | WO 94/26228 | 11/1994 |
| WO | WO 95/05781 | 3/1995 |
| WO | WO 95/09570 | 4/1995 |
| WO | WO 95/17222 | 6/1995 |
| WO | WO 96/34571 | 11/1996 |
| WO | WO 97/05829 | 2/1997 |
| WO | WO 97/05829 A1 | 2/1997 |
| WO | WO 97/16127 | 5/1997 |
| WO | WO 98/14131 | 4/1998 |
| WO | WO 98/38932 A1 | 9/1998 |
| WO | WO 99/03414 | 1/1999 |
| WO | WO 99/20213 A1 | 4/1999 |
| WO | WO 99/58070 A2 | 11/1999 |
| WO | WO 99/66850 A1 | 12/1999 |
| WO | WO 00/78240 A1 | 12/2000 |
| WO | WO 01/26570 A1 | 4/2001 |
| WO | WO 01/28444 A1 | 4/2001 |
| WO | WO 01/35845 A1 | 5/2001 |
| WO | WO 01/60273 A1 | 8/2001 |
| WO | WO 01/66026 A2 | 9/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

OTHER PUBLICATIONS

Carter, James, "Suture? Staple? Electrosugery? How to Decide What is Best for You", JSLS., Apr.-Jun., 1997; 1(2): pp. 171-174.

Matek et al., "Modified Electrocoagulation and Its Possibilities in the Control of Gastrointestinal Bleeding", Endoscopy., Nov. 1979; 11(4): pp. 253-258.

Mittleman et al., "Use of the Saline Infusion Electrode Catheter for Improved Energy Delivery and Increased Lesion Size in Radiofrequency Catheter Ablation", PACE., May 1995; 18(5 Pt 1): pp. 1022-1027.

Sakatani et al., "Isotonic Mannitol and the Prevention of Local Heat Generation and Tissue Adherence to Bipolar Diathermy Forceps Tips during Electrical Coagulation", J. Neurosurg., Apr. 1995; 82(4): pp. 669-671.

Takao, T., "Effect of Cautery with Irrigation Forceps on the Remnant Liver after Hepatectomy in Rats", Eur. Surg. Res., 1999; 31(2): pp. 173-179.

Yasargil, M.G., "Microsurgery Applied to Neurosurgery", New York: Academic Press, 1969, pp. 41-45.

Yamamoto et al., "New Simple Technique for Hepatic Parenchymal Resection Using a Cavitron Ultrasonic Surgical Aspirator and Bipolar Cautery Equipped with a Channel for Water Dripping", World. J. Surg., Oct. 1999; 23(10): pp. 1032-1037.

U.S. Office Action issued in related U.S. Appl. No. 11/318,207, dated Dec. 30, 2008.
U.S. Office Action issued in related U.S. Appl. No. 10/488,801, dated Dec. 2, 2008.
European Search Report dated Jun. 24, 2008 issued in related European Patent Application No. 08153786.2-2305.
European Office Action dated Oct. 14, 2008 issued in related European Patent Application No. 08153786.2-2305.
U.S. Office action issued in related U.S. Appl. No. 10/265,170, dated Jan. 12, 2009.
European Office Action dated Feb. 20, 2009 issued in related European Patent Application No. 02798936.7.
European Office Action dated May 6, 2009 issued in related European Patent Application No. 05851938.0.
European Office Action dated Nov. 25, 2008 issued in related European Patent Application No. 05851938.0.
Office Action dated Jul. 17, 2009 recieved in related U.S. Appl. No. 11/274,908.
United States Office Action dated Aug. 4, 2009 issued in related U.S. Appl. No. 11/537,852.
Office Action dated Jul. 2, 2009 issued in related U.S. Appl. No. 10/813,736.
Office Action dated Sep. 8, 2009 issued in related U.S. Appl. No. 10/488,801.
Office Action dated Sep. 15, 2009 issued in related U.S. Appl. No. 10/365,170.
Office Action dated Dec. 24, 2009 issued in related U.S. Appl. No. 10/813,736.
Office Action dated Apr. 26, 2010 issued in related U.S. Appl. No. 11/537,852.
Office Action dated Apr. 5, 2010 issued in related U.S. Appl. No. 11/318,207.
Office Action dated Mar. 18, 2010 issued in related U.S. Appl. No. 10/365,170.
Notice of Allowance dated Apr. 2, 2010 issued in related U.S. Appl. No. 11/274,908.
Supplemental Notice of Allowance dated Apr. 26, 2010 issued in related U.S. Appl. No. 11/274,908.
Office Action dated Jan. 29, 2010 issued in related U.S. Appl. No. 10/488,801.
Office Action dated Apr. 14, 2009 issued in related U.S. Appl. No. 10/547,881.
Office Action dated Sep. 17, 2009 issued in related U.S. Appl. No. 11/318,207.
Office Action dated Jun. 22, 2009 issued in related U.S. Appl. No. 11/486,807.
Office Action dated Jul. 12, 2010 issued in related U.S. Appl. No. 10/746,22.

* cited by examiner

FLUID DELIVERY SYSTEM AND CONTROLLER FOR ELECTROSURGICAL DEVICES

CROSS REFERENCE TO RELATED APPLICATIONS

This application is a continuation of U.S. application Ser. No. 09/797,049, filed Mar. 1, 2001, now U.S. Pat. No. 6,702,810, which claimed priority under 35 U.S.C. 119(e) to U.S. provisional application Ser. No. 60/187,114, filed Mar. 6, 2000.

FIELD OF THE INVENTION

This invention relates to the field of devices for use in operative surgery upon tissues of the body. More particularly, the invention relates to electrosurgical methods and systems for treatment of body tissues.

BACKGROUND OF THE INVENTION

Electrosurgical devices use electrical energy, most commonly radio frequency (RF) energy, to cut tissue or to cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to stop the bleeding from severed blood vessels.

Current electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 320° C., and such high temperatures can be transmitted to adjacent tissue via thermal diffusion. Undesirable results of such transmission to adjacent tissue include unintended thermal damage to the tissue.

Using saline to couple RF electrical energy to tissue prevents such undesirable effects as sticking, desiccation, smoke production and char formation. One key factor is preventing tissue desiccation, which occurs if tissue temperature exceeds 100° C. and all of the intracellular water boils away, leaving the tissue extremely dry and much less electrically conductive. However, an uncontrolled flow rate of saline can provide too much cooling at the electrode/tissue interface. This cooling reduces the temperature of the target tissue being treated, and the rate at which tissue thermal coagulation occurs is determined by tissue temperature. This, in turn, can result in longer treatment time, to achieve the desired tissue temperature for cauterization or cutting of the tissue. Long treatment times are undesirable for surgeons since it is in the best interest of the patient, physician and hospital to perform surgical procedures as quickly as possible.

RF energy delivered to tissue is unpredictable and often not optimal when using general-purpose generators. Most general-purpose RF generators have modes for different waveforms (cut, coagulation, or a blend of these two) and device types (monopolar, bipolar), as well as power levels that can be set in watts. However, once these settings are chosen, the actual power delivered to tissue can vary dramatically over time as tissue impedance changes over the course of RF treatment. This is because the power delivered by most generators is a function of tissue impedance, with the power ramping down as impedance either decreases toward zero or increases significantly to several thousand ohms.

A further limitation of current electrosurgical devices arises from size constraints of the device in comparison to tissue that is encountered during a single surgical procedure. During the course of a single procedure, for example, a surgeon often encounters a wide variety of tissue sizes. Surgical devices often come in a variety of sizes because larger segments of tissue physically require commensurately larger electrode jaws or tips, but smaller segments of tissue often are not optimally treated by the much larger size RF device. It is undesirable to require numerous surgical devices during a single procedure, because this wastes valuable operating room time, can make it difficult to precisely relocate the treatment site, increases the risk of infection, and increases the cost by increasing the number of different surgical devices that are needed to complete the surgical procedure.

For example, a bipolar saline-enhanced tissue sealing forceps that has jaws long enough to effectively seal a 30 mm length of tissue may not be desirable for sealing a segment of tissue that is 10 mm in length. Excess saline from one of the electrode jaws (for a bipolar device) can flow to the other electrode in the space where there is no intervening tissue. This flow of electrically conductive saline can act as an electrical resistor in parallel with the electrical pathway through the target tissue. Electrical current flow through the saline can divert or shunt RF energy away from going through the target tissue, and slow down the rate at which the target tissue is heated and treated.

A surgeon may first be sealing and cutting lung tissue as part of a wedge resection using the full 30 mm jaw length 2-3 times to remove a tip of a lobe of lung for biopsy. If the intraoperative histopathology indicates that the suspected tissue has a malignant tumor, then the surgeon may convert the procedure to a lobectomy. As part of the lobectomy the surgeon will want to seal and cut large blood vessels that supply the lobe. Alternatively, the surgeon may want to toughen up or coagulate large vessels with RF and then apply a ligating clip to assure hemostasis before cutting. Even compressed, these blood vessels might only fill a small fraction of the 30 mm length of electrode jaw. For at least the reasons identified above, this is an undesirable situation with current electrosurgical devices.

SUMMARY OF THE INVENTION

The invention provides a system for treating tissue comprising a power measurement device, a flow rate controller coupled to the power measurement device, and an electrosurgical device configured and arranged to provide radio frequency power and conductive fluid to the tissue, wherein the flow rate controller is configured and arranged to modify a flow rate of the conductive fluid to the tissue, based on signals from the power measurement device.

Preferably, the flow rate controller modifies the flow rate of the conductive fluid to the tissue based on heat used to warm the conductive fluid and heat used to convert the conductive fluid to vapor. In a preferred embodiment, the flow rate controller modifies the flow rate of the conductive fluid to the tissue using the relationship:

$$K = \frac{1}{\{\rho c_p \Delta T + \rho h_v Q_b / Q_l\}}$$

In another embodiment, the invention provides a device for modifying flow rate of conductive fluid to tissue based on measurement of radio frequency power delivered to the tissue, the device comprising a flow rate controller configured and arranged to modify flow rate of the conductive fluid to the tissue, based on heat used to warm the conductive fluid and heat used to convert the conductive fluid to vapor. Preferably, the device modifies the flow rate of the conductive fluid to the tissue using the relationship:

$$K = \frac{1}{\{\rho c_p \Delta T + \rho h_v Q_b / Q_l\}}$$

In an alternative embodiment, the invention provides a device for treating tissue using radio frequency power and conductive fluid, the device comprising a sensing device, and a processor coupled to the sensing device, wherein the processor is configured and arranged to adjust flow rate of the conductive fluid to the tissue, by determining a level of radio frequency power applied to the tissue using the sensing device, and adjusting the flow rate of the conductive fluid to the tissue. Preferably, the processor is configured and arranged to adjust the flow rate of the conductive fluid to the tissue based on heat used to warm the conductive fluid and heat used to convert the conductive fluid to vapor. Preferably, the flow rate controller modifies the flow rate of the conductive fluid to the tissue using the relationship:

$$K = \frac{1}{\{\rho c_p \Delta T + \rho h_v Q_b / Q_l\}}$$

In another embodiment, the invention provides a method for treating tissue comprising applying radio frequency power and conductive fluid to the tissue using a surgical device, wherein the conductive fluid is provided to the tissue at a fluid flow rate, determining an amount of radio frequency power applied to the tissue, and modifying the fluid flow rate based on the power applied to the tissue. Preferably, the step of modifying the fluid flow rate based on the power applied to the tissue comprises modifying the flow rate of the conductive fluid to the tissue based on heat used to warm the conductive fluid and heat used to convert the conductive fluid to vapor. Preferably, the step of modifying the fluid flow rate based on the power applied to the tissue comprises determining the fluid flow rate using the relationship:

$$K = \frac{1}{\{\rho c_p \Delta T + \rho h_v Q_b / Q_l\}}$$

In an alternative embodiment, the invention provides a method for treating tissue comprising providing a surgical device comprising an electrode, wherein the surgical device is configured and arranged to receive radio frequency power and conductive fluid and deliver the radio frequency power and conductive fluid to the tissue, determining the radio frequency power applied to the tissue, and providing the conductive fluid to the tissue at a fluid flow rate, wherein the fluid flow rate is modified to control boiling of the conductive fluid at the tissue. Preferably, the step of providing the conductive fluid to the tissue at a fluid flow rate comprises providing the conductive fluid to the tissue based on heat used to warm the conductive fluid and heat used to convert the conductive fluid to vapor. In a preferred embodiment, the step of providing the conductive fluid to the tissue at a fluid flow rate comprises providing the conductive fluid to the tissue using the relationship:

$$K = \frac{1}{\{\rho c_p \Delta T + \rho h_v Q_b / Q_l\}}$$

In another embodiment, the invention provides a system for treating tissue comprising a power measurement device, a flow rate controller coupled to the power measurement device, a flow control device coupled to the flow rate controller, and an electrosurgical device coupled to the flow control device and the power measurement device, wherein the electrosurgical device is configured and arranged to provide radio frequency power and conductive fluid to the tissue, and wherein the flow rate controller is configured and arranged to modify a flow rate of the conductive fluid to the electrosurgical device, based on signals from the power measurement device. Preferably, the flow control device comprises a pump. In one embodiment, the pump comprises a peristaltic pump. In another embodiment, the pump comprises a syringe pump. Preferably, the electrosurgical device comprises a bipolar electrosurgical device.

According to this embodiment, the flow rate controller is preferably configured and arranged to modify the flow rate of the conductive fluid to the flow control device based on heat used to warm the conductive fluid and heat used to convert the conductive fluid to vapor. In a preferred embodiment, the flow rate controller is configured and arranged to modify the flow rate of the conductive fluid to the tissue using the relationship:

$$K = \frac{1}{\{\rho c_p \Delta T + \rho h_v Q_b / Q_l\}}$$

The invention can improve the speed of tissue coagulation provided by fluid-enhanced electrosurgery by assuring that the electrode-tissue interface is within a desired temperature range (for example, not significantly hotter than 100° C.) through the control of the fraction of conductive fluid that is boiled off at the electrode-tissue interface. This improvement can be achieved by measuring power provided to the device and regulating the flow of fluid to the device. Preferably, tissue sensors (for example, that would measure tissue temperature or tissue impedance) are not required according to the invention.

Some embodiments of the invention can provide one or more advantages, such as the ability to achieve the desired tissue effect (for example, coagulation, cutting, or the like) in a fast, effective manner. The invention can also provide the ability to treat tissue quickly without using a tissue sensor (for example, a temperature sensor) built into the device or a custom special-purpose generator. The invention can allow a surgeon to use a variety of electrosurgical devices with a wide variety of general-purpose generators. Further, the invention can provide the ability to use an electrosurgical device that is capable of quickly and effectively sealing a wide variety of tissue sizes and thicknesses.

DETAILED DESCRIPTION OF THE PREFERRED EMBODIMENTS

Overview

The invention provides a system, device and methods that preferably improve control of tissue temperature at a treatment site during a medical procedure. The invention is particularly useful during surgical procedures upon tissues of the body, where tissue is often cut and coagulated. The invention involves the use of electrosurgical procedures, which utilize RF power and conductive fluid to treat tissue. Preferably, a desired tissue temperature range is achieved through, adjusting parameters, such as conductive fluid flow rate, that affect the temperature at the tissue/electrode interface. Preferably, the device achieves a desired tissue temperature utilizing a desired percentage boiling of the conductive solution at the tissue/electrode interface. In a preferred embodiment, the invention provides a control device, the device comprising a flow rate controller that receives a signal indicating power applied to the system, and adjusts the flow rate of conductive fluid from a fluid source to an electrosurgical device. The invention also contemplates a control system comprising a flow rate controller, a measurement device that measures power applied to the system, and a pump that provides fluid at a desired flow rate.

Figure 1:
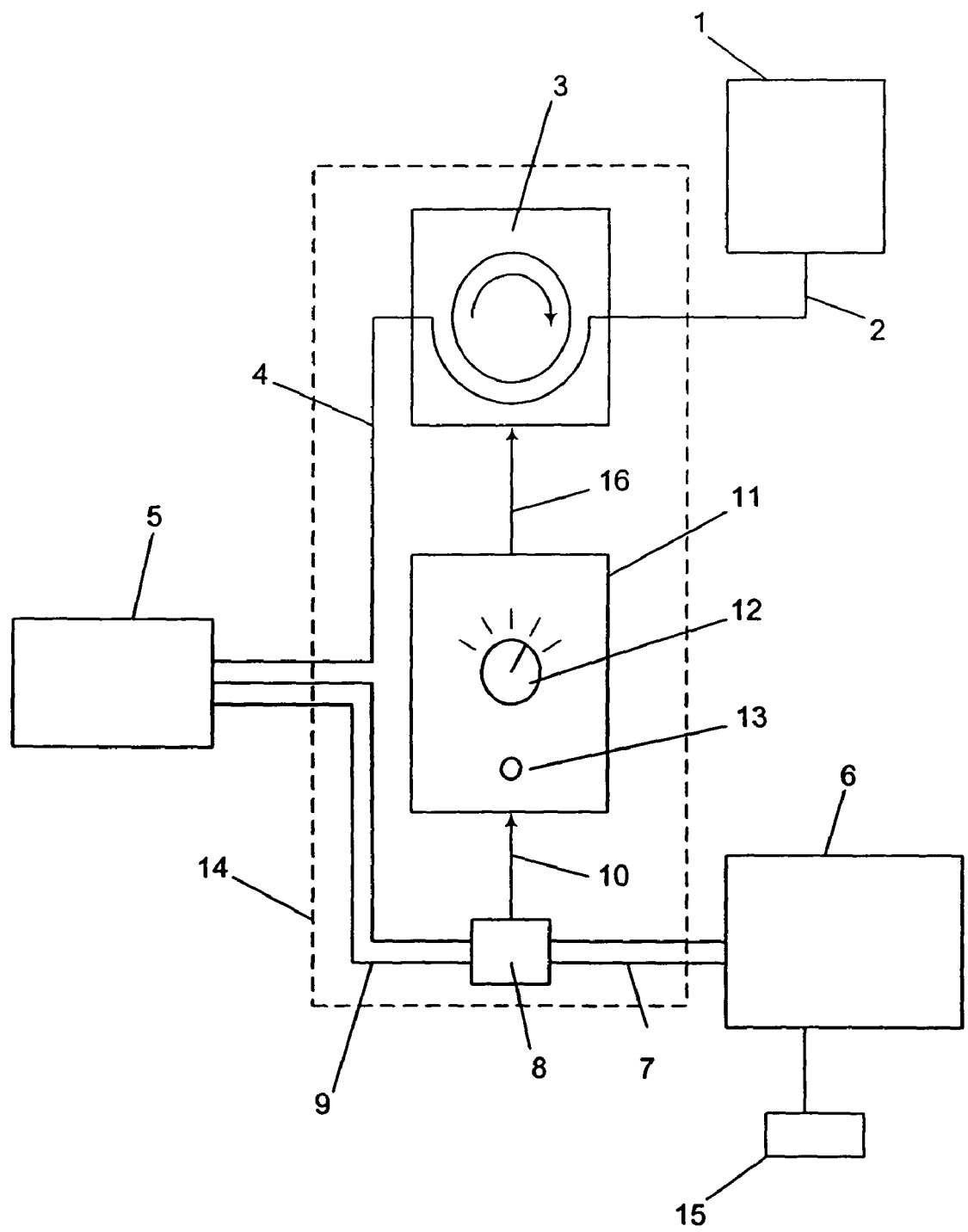
FIG. 1 is a block diagram showing one embodiment of the overall control system of the invention, and an electrosurgical device.

The invention will be discussed generally with reference to FIG. 1. FIG. 1 shows a block diagram of one embodiment of a system of the invention. As shown in FIG. 1, conductive fluid is provided from a fluid source 1, through a fluid line 2, to a pump 3, which has an outlet fluid line 4 that is connected to an electrosurgical device 5. In a preferred embodiment, the conductive fluid comprises saline, such as sterile, normal saline. Although the description herein will describe saline as a conductive fluid, one of skill in the art would understand, upon reading this disclosure, that other conductive fluids can be used in accordance with the invention. The conductive fluid can comprise physiologic saline ("normal" saline, or 0.9% NaCl solution), lactated Ringer's™, or the like.

A generator 6 provides RF energy via a cable 7 to a power measurement device 8 that measures the RF electrical power. In this embodiment, the power measurement device 8 does not turn the power off or on or alter the power in any way. A power switch 15 connected to the generator 6 is provided by the generator manufacturer and is used to turn the generator 6 on and off. The power switch 15 can comprise any switch to turn the power on and off, and is commonly provided in the form of a footswitch or other easily operated switch. A cable 9 carries RF energy from the power measurement device 8 to the electrosurgical device 5. Power is preferably measured before it reaches the electrosurgical device.

A flow rate controller 11 includes a selection switch 12 that can be set to achieve desired levels of percentage fluid boiling (for example, 100%, 98%, 80% boiling). The flow rate controller 11 receives a signal 10 from the power measurement device 8 and calculates the correct fluid flow rate based on percentage boiling indicated by the selection switch 12. In a preferred embodiment, a fluid switch 13 is provided so that the fluid system can be primed (air eliminated) before turning the generator 6 on. The output signal 16 of the flow rate controller 11 is sent to the pump 3 motor to regulate the flow rate of conductive fluid, and thereby provide an appropriate fluid flow rate for the amount of power being delivered.

Throughout the present description, like reference numerals and letters indicate corresponding structure throughout the several views, and such corresponding structure need not be separately discussed.

In one embodiment, the invention comprises a flow rate controller that is configured and arranged to be connected to a source of RF power, and a source of conductive fluid. The device of the invention receives information about the level of RF power applied to an electrosurgical device, and adjusts the flow rate of the conductive fluid to the electrosurgical device, thereby controlling temperature at the tissue treatment site.

In another embodiment, elements of the system are physically included together in one electronic enclosure. One such embodiment is shown by enclosure within the outline box 14 of FIG. 1. In the illustrated embodiment, the pump 3, flow rate controller 11, and power measurement device 8 are enclosed within an enclosure, and these elements are connected through electrical connections to allow signal 10 to pass from the power measurement device 8 to the flow rate controller 11, and signal 16 to pass from the flow rate controller 11 to the pump 3. Other elements of a system can also be included within one enclosure, depending upon such factors as the desired application of the system, and the requirements of the user.

The pump 3 can be any suitable pump used in surgical procedures to provide saline or other fluid at a desired flow rate. Preferably, the pump 3 comprises a peristaltic pump. Alternatively, pump 3 can be a "syringe pump," with a built-in fluid supply; or a double-acting syringe pump with two syringes such that they can draw saline from a reservoir. Conductive fluid can also be provided from an intravenous ("I.V.") bag full of saline that flows under the influence of gravity to the pump 3. Similar pumps can be used in connection with the invention, and the illustrated embodiments are exemplary only. The precise configuration of the pump 3 is not critical to the invention. In some embodiments, the pump can be substituted with any type of flow controller, to allow the user to control the flow rate of conductive fluid to the device. Alternatively, a valve configuration can be substituted for pump 3.

The components of the system will now be described in detail.

The Flow Rate Controller

The flow rate controller 11 controls the rate of flow from the fluid source 1, based upon the amount of RF power provided from the generator 6 to the electrosurgical device 5. The flow rate of conductive fluid, such as saline, interacts with the RF power and various modes of heat transfer away from the target tissue, as described herein.

Figure 2:
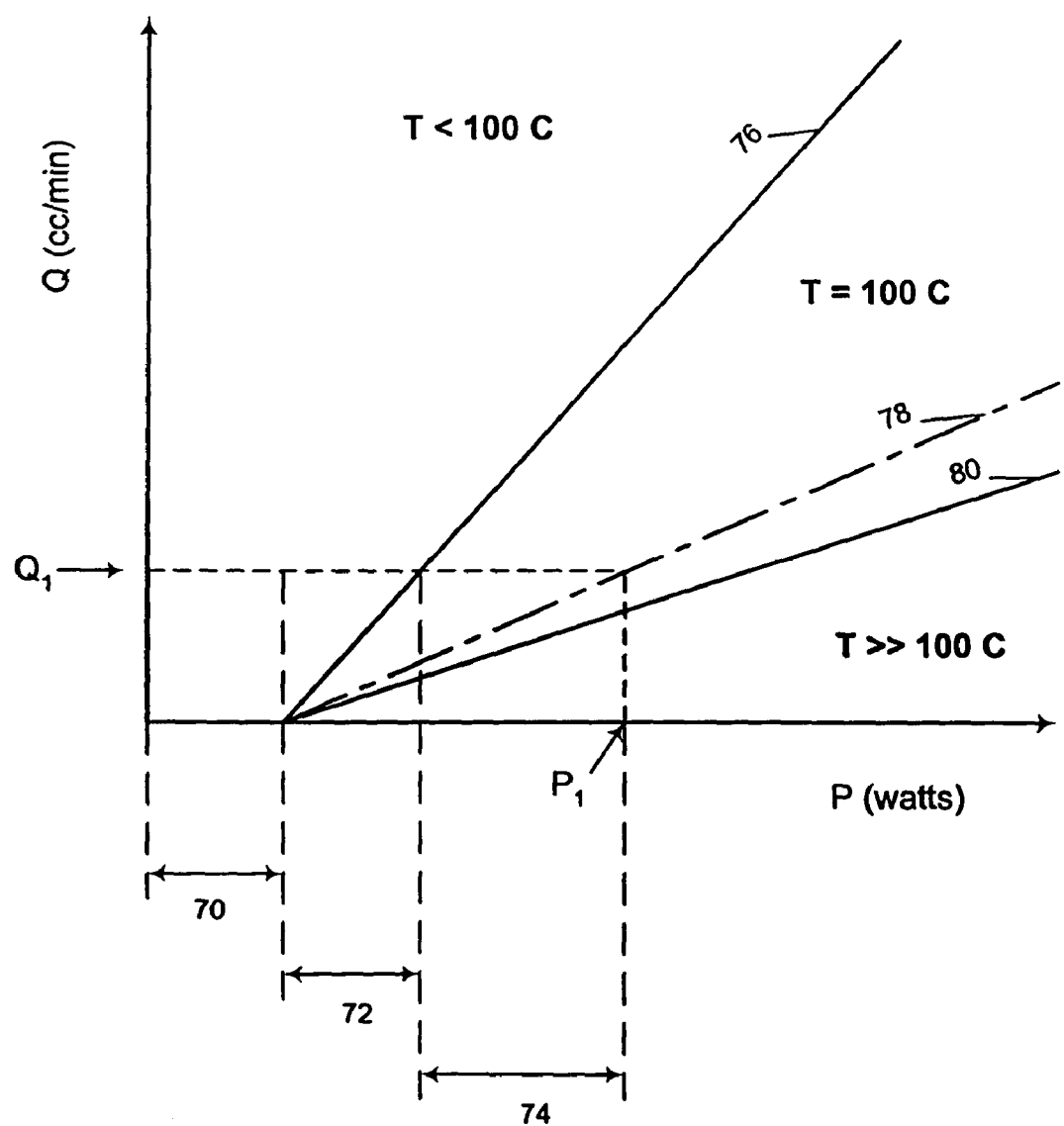
FIG. 2 is a schematic graph that describes the relationship between RF power to tissue (P), flow rate of saline (Q), and tissue temperature (T).

FIG. 2 shows a schematic graph that describes the relationship between the flow rate of saline, RF power to tissue, and regimes of boiling. Based on a simple one-dimensional lumped parameter model of the heat transfer, the peak tissue temperature can be estimated, and once tissue temperature is estimated, it follows directly whether it is hot enough to boil saline.

$$P = \Delta T/R + \rho c_p Q_l \Delta T + \rho Q_b h_v \quad (1)$$

Where P=the total RF electrical power that is converted into heat.

Conduction. The first term [$\Delta T/R$] in equation (1) is heat conducted to adjacent tissue, represented as 70 in FIG. 2, where:

$\Delta T = (T - T_\infty)$ the difference in temperature between the peak tissue temperature (T) and the normal temperature ($T_\infty$) of the body tissue (° C.). Normal temperature of the body tissue is generally 37° C.; and R=Thermal Resistance of surrounding tissue, the ratio of the temperature difference to the heat flow (° C./watt).

This thermal resistance can be estimated from published data gathered in experiments on human tissue (Phipps, J. H., "Thermometry studies with bipolar diathermy during hysterectomy," *Gynaecological Endoscopy*, 3:5-7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320-37)/50 = 5.7 \approx 6° C./watt$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than 100° C. to prevent desiccation of the tissue. Assuming that saline boils at 100° C., the first term in equation (1) ($\Delta T/R$) is equal to (100−37)/6=10.5 watts. Thus, based on this example, the maximum amount of heat conducted to adjacent tissue without any significant risk of tissue desiccation is 10.5 watts.

Referring to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection. The second term [$\rho c_p Q_l \Delta T$] in equation (1) is heat used to warm up the flow of saline without boiling the saline, represented as 72 in FIG. 2, where:

ρ=Density of the saline fluid that gets hot but does not boil (approximately 1.0 gm/cm³);

$c_p$=Specific heat of the saline (approximately 4.1 watt-sec/gm-° C.);

$Q_l$=Flow rate of the saline that is heated (cm³/sec); and $\Delta T$=Temperature rise of the saline. Assuming that the saline is heated to body temperature before it gets to the electrode, and that the peak saline temperature is similar to the peak tissue temperature, this is the same $\Delta T$ as for the conduction calculation above.

The onset of boiling can be predicted using equation (1) with the last term on the right set to zero (no boiling) ($\rho Q_b h_v = 0$), and solving equation (1) for $Q_l$ leads to:

$$Q_l = [P - \Delta T/R]/\rho c_p \Delta T \quad (2)$$

This equation defines the line shown in FIG. 2 as the line of onset of boiling 76. It is possible in some embodiments that the flow of conductive fluid can be nonuniformly heated, thereby reducing the term in the denominator of Equation (2), $\rho c_p \Delta T$. If the amount of convection is less due to nonuniformity of heating, conductive fluid boiling would occur sooner. In other words, the slope of the curve will be steeper at a given power, and conductive fluid will boil at a lower flow rate. This type of nonuniformity can be associated with device configurations and hence could be used to provide a level of control of convection. For example, for a particular type of device known to provide nonuniform heating of the conductive solution, the invention can provide an "offset" to take this into account to provide the desired level of boiling at the electrode/tissue interface.

Boiling. The third term [$\rho Q_b h_v$] in equation (1) relates to heat that goes into converting liquid saline to vapor saline and is represented as 74 in FIG. 2, where:

$Q_b$=Flow rate of saline that boils (cm³/sec); and $h_v$=Heat of vaporization of saline (approximately 2,000 watt-sec/gm).

A flow rate of only 1 cc/min will absorb a significant amount of heat if it is completely boiled, or about $\rho Q_b h_v = (1)$ (1/60) (2,000)=33.3 watts. The heat needed to warm this flow rate from body temperature to 100° C. is much less, or $\rho c_p Q_l \Delta T = (1)(4.1)(1/60)(100-37) = 4.3$ watts. In other words, the most significant factor contributing to heat transfer from a wet electrode device can be fractional boiling. The present invention recognizes this fact and exploits it.

Fractional boiling can be described by equation (3) below:

$$Q_l = \frac{\{P - \Delta T/R\}}{\{\rho c_p \Delta T + \rho h_v Q_b / Q_l\}} \quad (3)$$

If the ratio of $Q_b/Q_l$ is 0.50 this is the 50% boiling line 78 shown in FIG. 2. If the ratio is 1.0 this is the 100% boiling line 80 shown in FIG. 2.

Control Strategy

Figure 3:
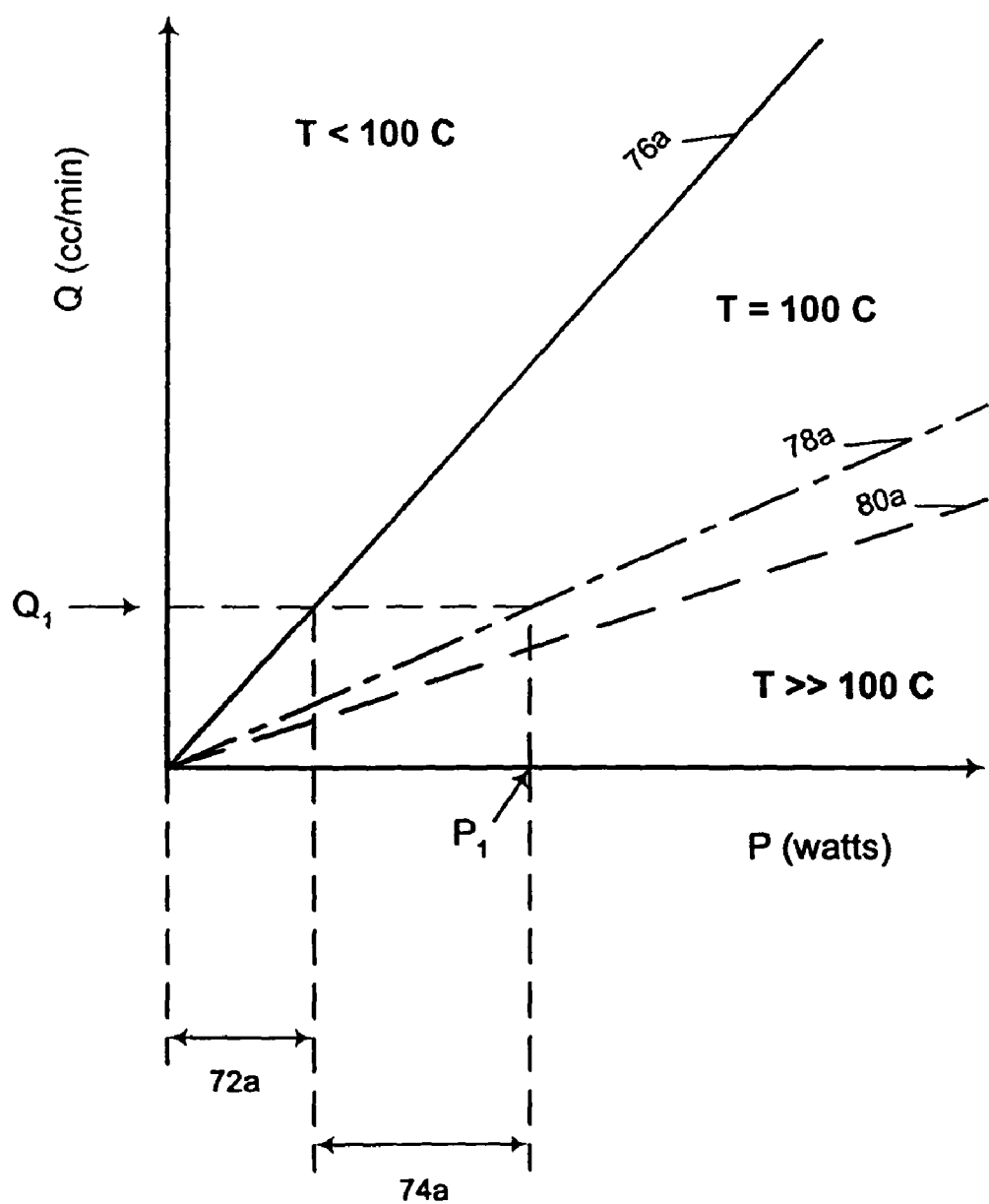
FIG. 3 is schematic graph that describes the relationship between RF power to tissue (P), flow rate of saline (Q), and tissue temperature (T) when heat conduction to adjacent tissue is neglected.

Since the amount of heat conducted away to adjacent tissue is difficult to precisely predict, it is preferable, from a control point of view, to assume the worst case situation of zero heat conduction, and provide enough saline so that if necessary, all the RF power could be used to heat up and boil the saline, thus providing that the peak tissue temperature will not go over 100° C. a significant amount. This situation is shown in the schematic graph of FIG. 3.

It is desirable to control the saline flow rate so that it is always on a "line of constant % boiling" for consistent tissue effect. If the device is monopolar and shunting through saline is not an issue, then it can be preferable to operate close to, but not over the line of the onset of boiling, 76a in FIG. 3. This preferably keeps tissue as hot as possible with causing desiccation. Alternatively, if the device is bipolar and shunting of electrical energy through excess saline is an issue, then it can be preferable to operate along a line of constant boiling such as line 78a in FIG. 3, the 50% line. This simple proportional control will have the flow rate determined by equation (4), where K is the proportionality constant:

$$Q_l = K \times P \quad (4)$$

In essence, when power P goes up, the flow rate Q will be proportionately increased. Conversely, when power P goes down, the flow rate Q will be proportionately decreased.

K is primarily dependent on the fraction of saline that boils, as shown in equation (5), which is equation (3) solved for K after eliminating P using equation (4), and neglecting the conduction term ($\Delta T/R$):

$$K = \frac{1}{\{\rho c_p \Delta T + \rho h_v Q_b / Q_l\}} \quad (5)$$

Thus, the present invention provides a method of controlling boiling of conductive fluid at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

Figure 4:
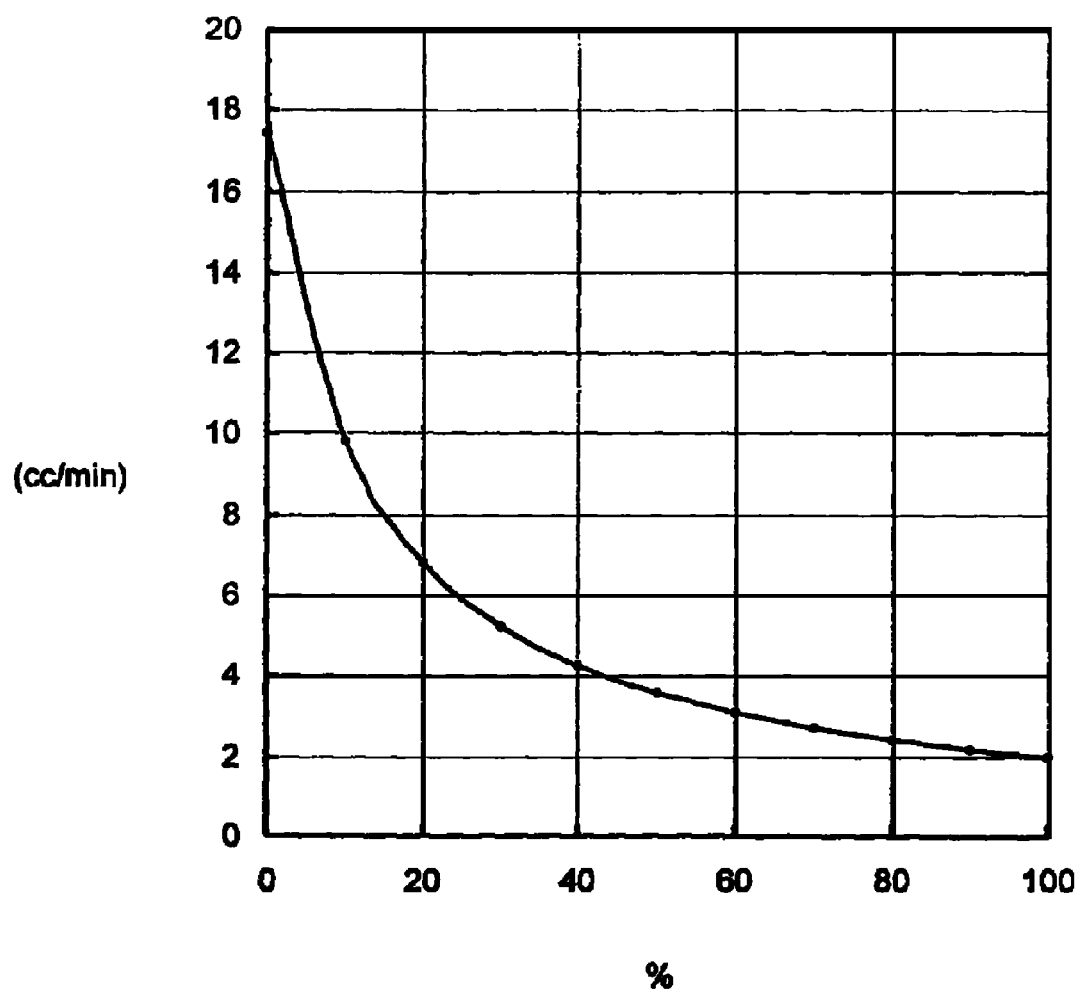
FIG. 4 is a graph showing the relationship of percentage saline boiling and saline flow rate (cc/min) for an exemplary RF generator output of 75 watts.

FIG. 4 shows an exemplary graph of flow rate versus % boiling for a situation where the RF power is 75 watts. The percent boiling is represented on the X-axis, and the saline flow rate (cc/min) is represented on the Y-axis. According to this example, at 100% boiling the most desirable saline flow rate is 2 cc/min.

As discussed herein, RF energy delivery to tissue can be unpredictable and vary with time, even though the generator has been "set" to a fixed wattage.

Figure 5:
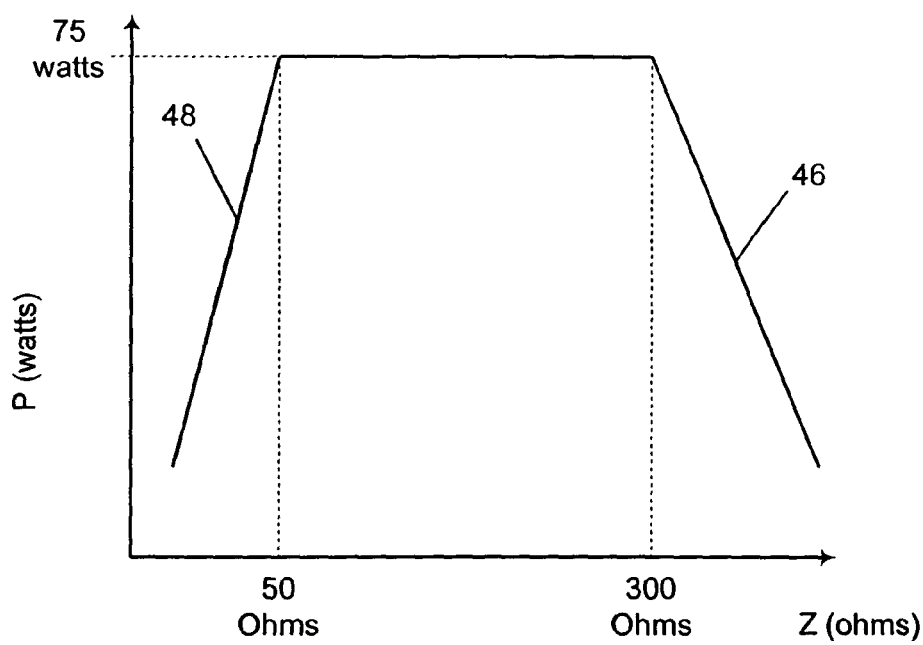
FIG. 5 is a schematic graph that describes the relationship of load impedance (Z, in ohms) and generator output power (P, in watts), for an exemplary generator output of 75 watts in a bipolar mode.

The schematic graph of FIG. 5 shows the general trends of the output curve of a typical general-purpose generator, with the output power changing as load (tissue plus cables) impedance changes. Load impedance (in ohms) is represented on the X-axis, and generator output power (in watts) is represented on the Y-axis. In the illustrated embodiment, the electrosurgical power (RF) is set to 75 watts in a bipolar mode. As shown in the figure, the power will remain constant as it was set as long as the impedance stays between two cut-offs of impedance, that is, between 50 ohms and 300 ohms in the illustrated embodiment. Below load impedance of 50 ohms, the power will decrease, as shown by the low impedance ramp 48. Above load impedance of 300 ohms, the power will decrease, as shown by the high impedance ramp 46. Of particular interest to saline-enhanced electrosurgery is the low impedance cut-off (low impedance ramp 48), where power starts to ramp down as impedance drops further.

Figure 6:
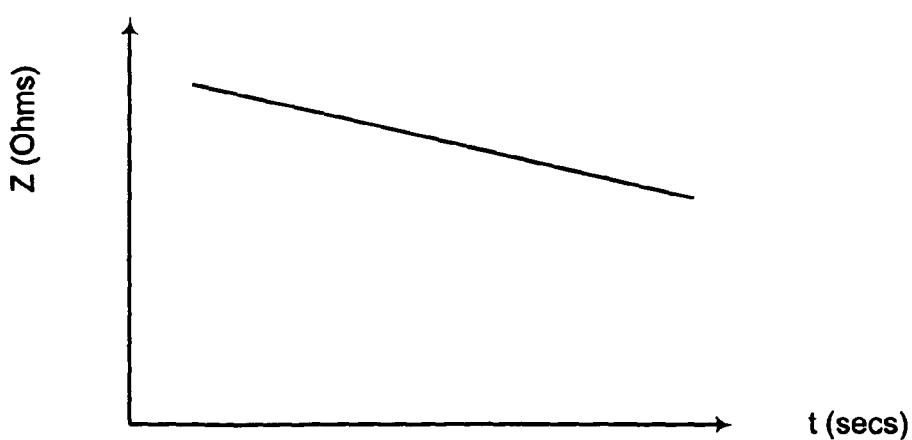
FIG. 6 is a schematic graph that describes the relationship of time (t, in seconds) and tissue impedance (Z, in ohms) after RF activation.

FIG. 6 shows the general trend of how tissue impedance generally changes with time for saline-enhanced electrosurgery. As tissue heats up, the temperature coefficient of the tissue and saline in the cells is such that the tissue impedance decreases. Thus, as tissue heats up, the load impedance decreases, approaching the impedance cut-off of 50 ohms. Once tissue is sufficiently heated, such that the impedance cut-off is passed, the power decreases along the lines of the low impedance ramp 48 of FIG. 5.

Combining the effects shown in FIG. 5 and FIG. 6, it becomes clear that when using a general-purpose generator set to a "fixed" power, the actual power delivered can change dramatically over time as tissue heats up and impedance drops. Looking at FIG. 5, if the impedance drops from 100 to 75 ohms over time, the power output would not change because the curve is "flat" in that region of impedances. If, however, the impedance drops from 75 to 30 ohms one would "turn the corner" onto the low impedance ramp 48 portion of the curve and the power output would decrease dramatically.

According to the invention, the control device receives a signal indicating the drop in actual power delivered to the tissue and adjusts the flow rate of saline to maintain the tissue/electrode interface at a desired temperature. In a preferred embodiment, the drop in actual power delivered is sensed by the power measurement device 8 (shown in FIG. 1), and the flow rate of saline is decreased by the flow rate controller 11 (also shown in FIG. 1). Preferably, this reduction in saline flow rate allows the tissue temperature to stay as hot as possible without desiccation. If the control device was not in operation and the flow rate allowed to remain higher, the tissue would be over-cooled at the lower power input. This would result in decreasing the temperature of the tissue at the treatment site.

The flow rate controller 11 of FIG. 1 can be a simple "hard-wired" analog or digital device that requires no programming by the user or the manufacturer. The flow rate controller 11 can alternatively include a processor, with or without a storage medium, in which the determination procedure is performed by software, hardware, or a combination thereof. In another embodiment, the flow rate controller 11 can include semi-programmable hardware configured, for example, using a hardware descriptive language, such as Verilog. In another embodiment, the flow rate controller 11 of FIG. 1 is a computer, microprocessor-driven controller with software embedded. In yet another embodiment, the flow rate controller 11 can include additional features, such as a mechanism to automatically keep the saline flow on for several seconds after the RF is turned off to provide a post-coagulation cooling of the tissue or "quench," which can increase the strength of the tissue seal.

As discussed herein, the saline can act as a shunt and divert energy away from target tissue. This is a phenomenon that can only occur with a bipolar device. In a monopolar device, saline can "pool" in the treatment area, and can, in some situations, divert energy by pooling. For the present discussion, shunting in connection with a bipolar device will be discussed.

In order to describe the underlying issue of saline shunting, an exemplary bipolar endoscopic electrosurgical device will be described in some detail. The bipolar electrosurgical device is described for purposes of illustrating the invention only, and it is understood that a wide variety of electrosurgical devices can be used in connection with the invention.

Preferably, the control device of the invention is used in connection with an electrosurgical device that is capable of controlling saline flow (for example, by controlling the location from which the saline is released from the electrosurgical device to the tissue). Any electrosurgical device that is capable of controlling saline flow is preferably used in connection with the invention described herein.

Figure 7:
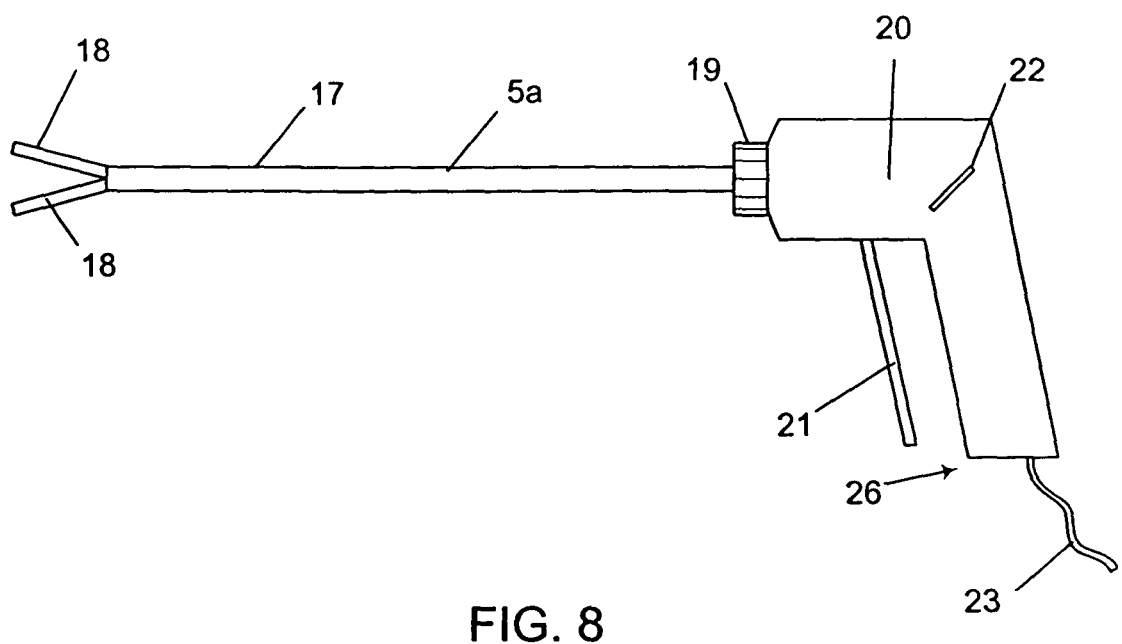
FIG. 7 is a schematic side view of one embodiment of a bipolar electrosurgical device.

FIG. 7 shows an overall simple side schematic view of one embodiment of an electrosurgical device 5a that is designed to grasp, coagulate and then cut tissue. The electrosurgical device 5a includes a shaft 17, two opposing jaws 18 at the distal tip of the shaft 17, a collar 19 for rotating the entire shaft, a proximal handle 20, an actuation lever 21 which when squeezed will close the opposing jaws 18, a pair of paddles 22 to activate the built-in cutting mechanism (not shown in the figure), and a cable 23 attached to the handle that contains two electrical wires and one fluid channel (not shown individually in the figure). In use, tissue to be treated is positioned between the jaws 18 of the device 5a. The actuation lever 21 is then moved in direction of arrow 26, thereby drawing the opposing jaws 18 toward each other, to close the jaws 18 on the tissue. RF energy and conductive fluid, such as saline, are applied through the device and to the treatment site, thereby heating the tissue to coagulate, or achieve the desired treatment of the tissue. If desired, after coagulating the tissue between the jaws, the jaws can be held clamped together and the cutting mechanism can be actuated to cut tissue.

Figure 8:
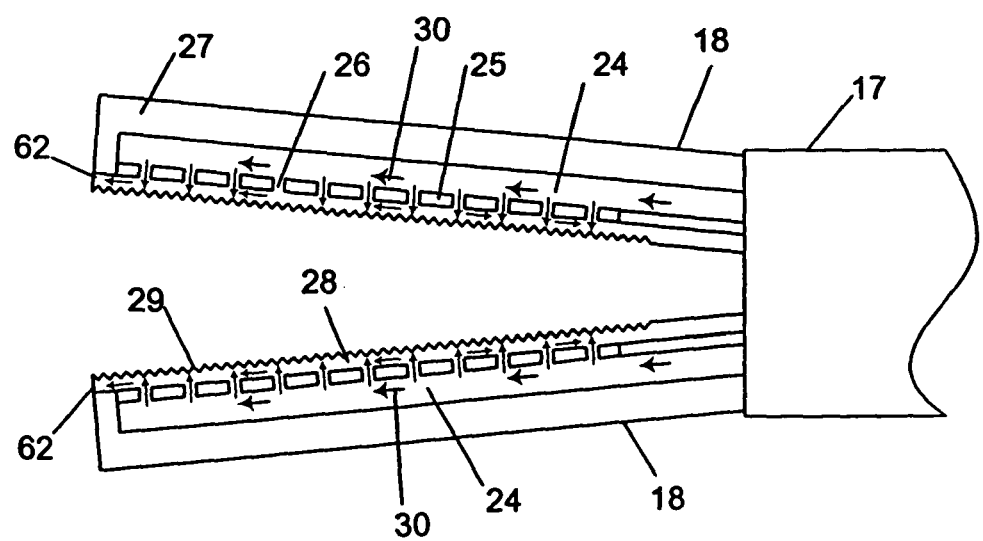
FIG. 8 is a schematic close-up section side view of the tip of the device shown in FIG. 7.

FIG. 8 shows a schematic close-up section view of the two jaws 18 at the distal tip of the shaft 17. In a preferred embodiment, each jaw 18 includes an electrode 25, a manifold 24, and a plurality of holes 26 in the electrode. Each jaw 18 further includes a jaw surface 29 that contacts the tissue to be treated. In the embodiment illustrated in FIG. 8, the jaw surface 29 is textured, so that it is capable of grasping the tissue to be treated. However, the jaw surface 29 need not be textured, and can include any type of desired surface configuration, such as serrations and the like, or can be provided with a smooth surface. In use, saline flows in a manifold 24 in the direction of arrows 30, wherein the manifold 24 distributes saline flow evenly to a plurality of holes 26 that are made in the jaw 18. Preferably, most of the structural material of each jaw 18 is fabricated from a material that is non-conductive electrically, such as nylon or other polymer such as liquid crystal polymer. This non-conductive material is shown in the figure as reference number 27. Further, in some embodiments, the jaw surface 29 can be fabricated from a nonconductive material. In a preferred embodiment, each jaw 18 further includes a groove 28 that is recessed from the jaw surface 29. In this embodiment, after the saline flows through the holes 26, it flows in the groove 28. When tissue is grasped between the jaws, saline can flow in the groove 28 between the electrode and the tissue, and exit through exit grooves 62 that are open to the outside at the proximal end of the jaws 18.

Figure 9:
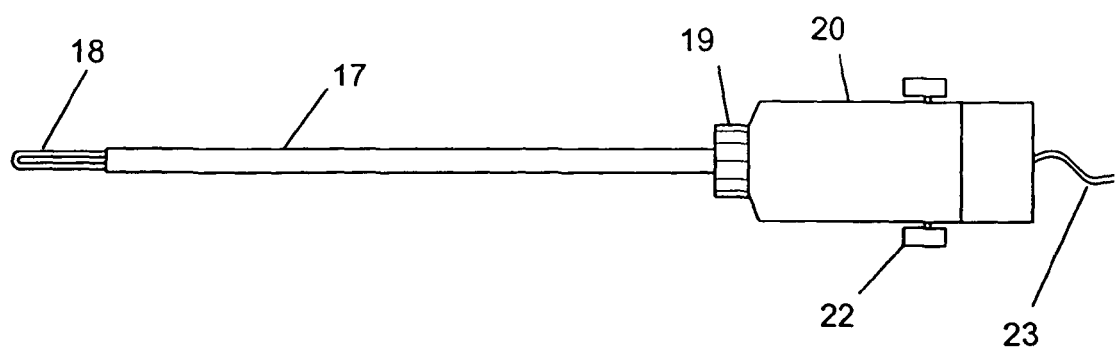
FIG. 9 is a schematic top view of the bipolar electrosurgical device shown in FIG. 7.
Figure 10:
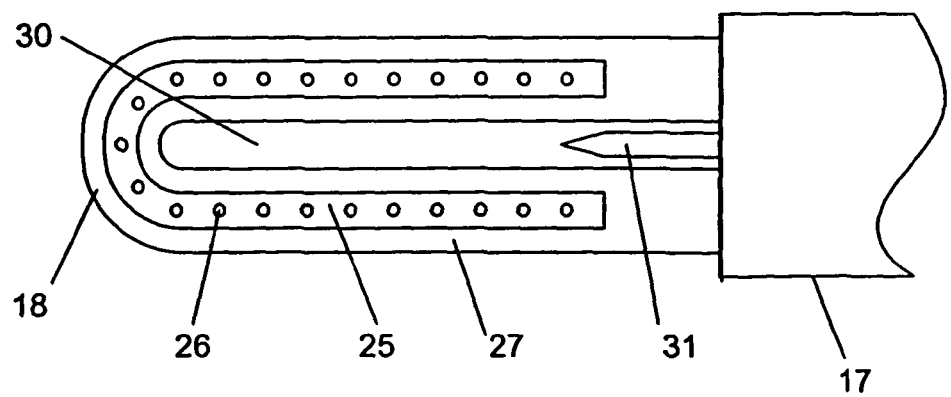
FIG. 10 is a schematic close-up section top view of the tip of the device shown in FIG. 9.

FIG. 9 shows an overall schematic top view of the electrosurgical device shown in FIGS. 7 and 8. As shown in FIG. 9, the jaws 18 can be provided in a loop configuration. FIG. 10 shows a close-up section of one of the loop jaws 18. In this embodiment, the jaws 18 are provided in a loop configuration to create a space 30 that allows a cutting mechanism 31 to move proximally and distally within the space 30. One of skill in the art would comprehend that the electrode configuration shown in FIG. 9 is simply an exemplary configuration, and the electrode need not be formed of two loops. For example, the electrosurgical device need not include a cutting mechanism, and the electrodes in these embodiments would not be required to include a space or recess for passage of the cutting mechanism. The invention contemplates any suitable electrode configuration used to treat tissue with RF energy and conductive fluid.

Figure 11:
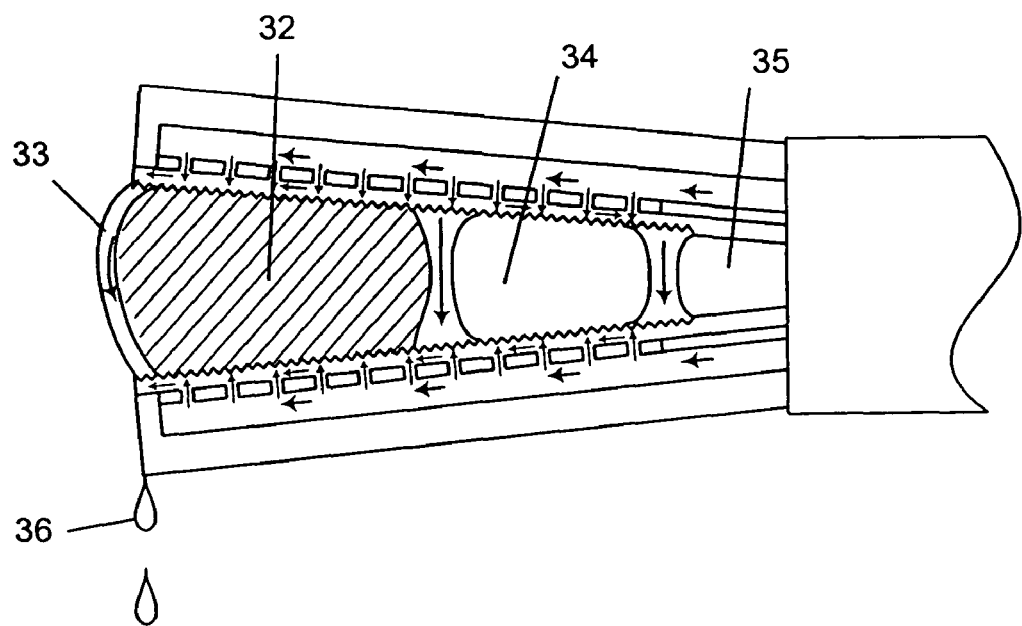
FIG. 11 is a schematic close-up section side view of the electrodes of the device shown in FIG. 9 showing saline shunting without boiling of the saline.

If the saline that flows from one electrode to the other is not boiling in any significant manner, a large fraction of the RF energy can be diverted away from target tissue. This "stealing" of RF energy tends to dramatically slow down the process of coagulating tissue and producing the desired hemostasis or aerostasis of the tissue. This situation is illustrated in FIG. 11. In this embodiment, tissue 32 grasped between the jaws 18 does not fill the jaws. Areas 34 and 35 show areas of air between the jaws 18. Saline liquid flows from the top electrode jaw to the lower electrode jaw in several locations: at area 33, located at the distal end of the jaws 18, at locations between tissue 32 and area 34, and between areas 34 and 35. These locations of saline flow between areas 34 and 35 represent the closest gap between jaws (area 35) and flow of saline along the tissue boundary 32, which are the most likely areas for saline flow between the jaws 18. Since most of the saline is not boiled, excess saline 36 drips off the lower jaw.

Figure 11A:
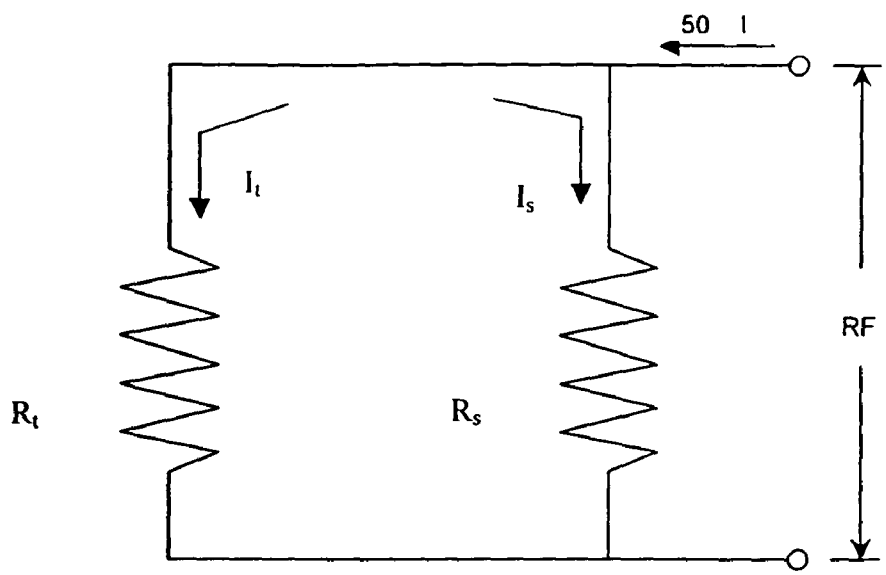
FIG. 11a is a diagram that describes the equivalent electrical circuit for tissue in parallel with a single saline shunt.

The saline shunting scenario can also be explained by using an electrical circuit as shown in FIG. 11a. Electrically, the tissue and the saline fluid shunt can be modeled as resistors in parallel. Using Ohm's Law one can calculate the percentage of total RF power that is dissipated in the saline shunt as:

$$\% \ RF \ \text{Power} = \frac{100}{[1 + R_s/R_t]}$$

Figure 11B:
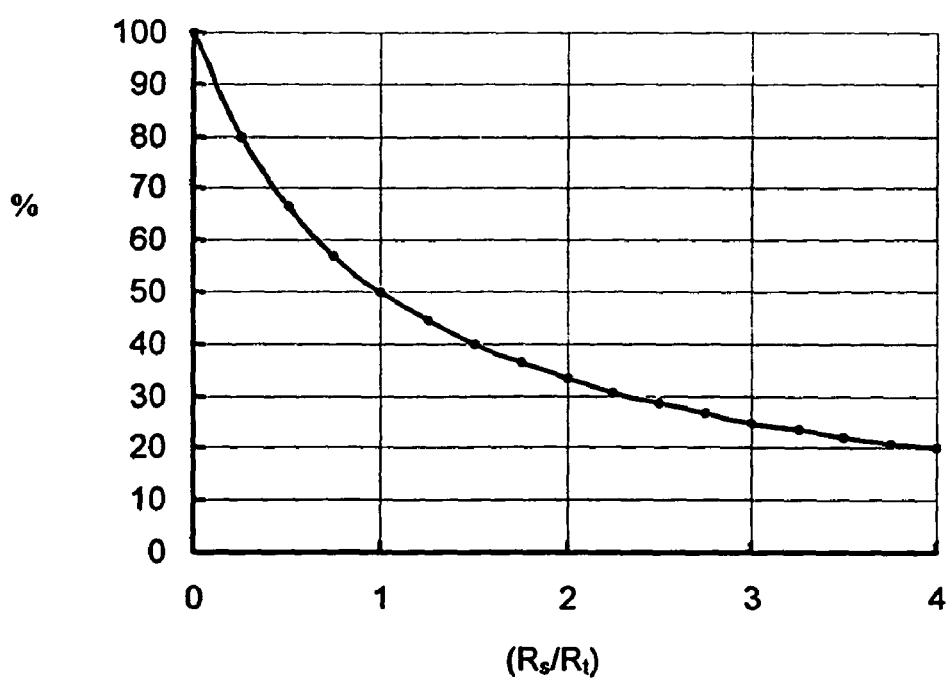
FIG. 11b is a graph that describes the relationship of ratio of saline to tissue resistance ($R_s/R_t$) and percent power shunted into saline.

In the embodiment illustrated in FIG. 11a, the total current (I) 50 from source 54 is split between two resistors, tissue electrical resistance ($R_t$), and saline shunt electrical resistance ($R_s$). This relationship is shown in the schematic graph of FIG. 11b, which shows the relationship of the ratio of saline to tissue resistance ($R_s/R_t$) to percent of power shunted into saline. As shown in the figure, when the resistance of the saline is equal to the tissue ($R_s/R_t=1$), half the power is shunted into the saline. For example, when the resistance of the saline is four times that of the tissue, then only 20% of the power is shunted into the saline.

Figure 12:
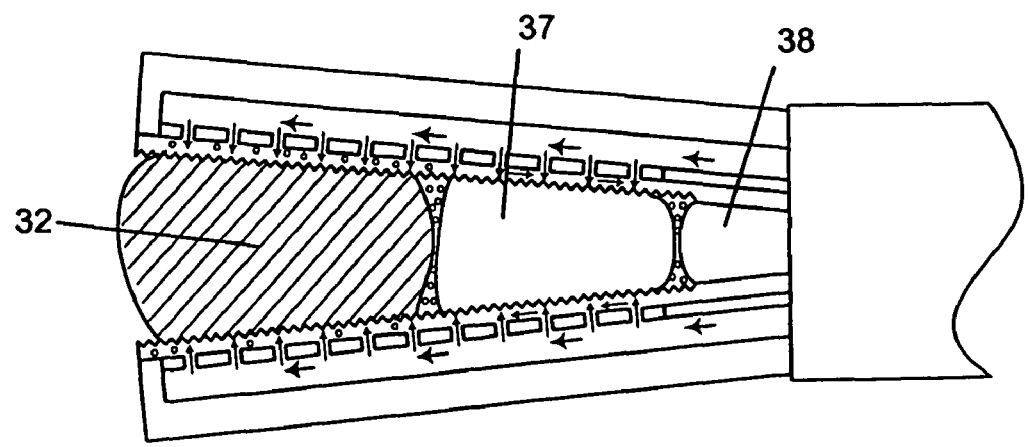
FIG. 12 is a schematic close-up side section view of the electrodes of the device shown in FIG. 9 showing a large percentage of the saline boiling at the tissue treatment site.

One benefit of the flow rate control strategy described herein, where a high % boiling is maintained, is that the flow of saline from one electrode to the other is either eliminated altogether because all the flow boils off at the electrode/tissue interface, or a large fraction of the flow boils as it flows toward the other electrode. This second case is illustrated in FIG. 12, that is, where a large fraction of the saline flow boils as it flows toward the other electrode. Note that in comparison to FIG. 11, there is less saline flowing from the top jaw to the lower jaw, and where there is flow it is actively boiling, as indicated by the vapor bubbles shown in several locations 37 and 38. According to the invention, boiling of a large fraction of the saline assures that most of the RF power will be directed into the tissue to achieve coagulation in the fastest time.

One aspect of the control strategy of the invention is that the flow of saline is preferably primarily directed spatially against or very near the target tissue that is to receive the RF power. If the flow rate is not near where the RF power is turned into heat, the saline is not capable of protecting the tissue from desiccation by dissipating excess heat in the boiling process. Therefore, in a preferred embodiment, the flow of conductive fluid is directly primarily at the tissue treatment site.

Use

Figure 13:
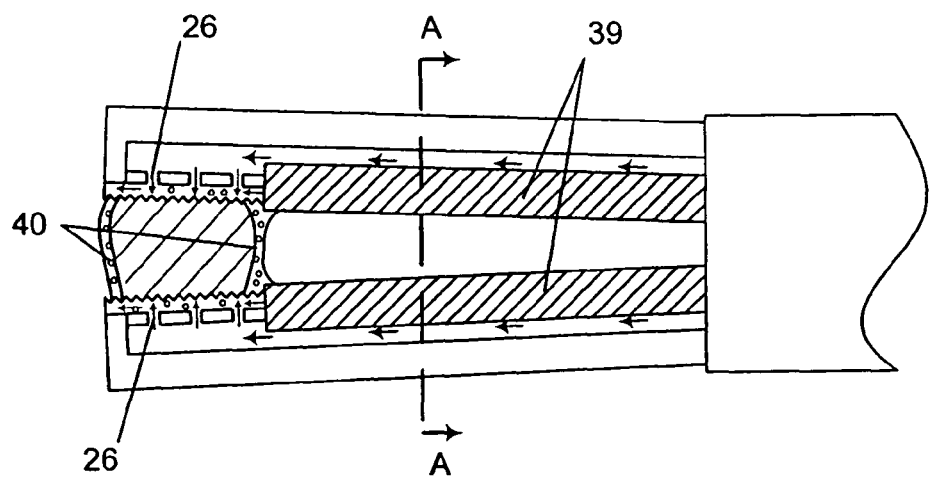
FIG. 13 is a schematic close-up side section view of electrodes of the device shown in FIG. 9 showing two gutters slid out to direct saline flow distally toward tissue.

Typically a surgeon will grasp a small amount of tissue with the very tip of the device as shown in FIG. 13. If the electrode jaws are long relative to the length of the tissue segment being grasped, then saline exiting of holes 26 in the proximal part of the jaws may not be able to flow to the tip, but may leak out along the upper jaw. Though surface tension will act to keep saline flow in the groove 28, gravity can tend to cause the saline collect and flow down directly to the opposing jaw. This would result in the undesirable effects mentioned above. By providing two slidable gutters 39, the flow of saline can be collected and directed distally toward the tissue. In this embodiment, the saline can flow from one jaw to the other in areas 40, located on each side of the tissue being grasped, but with a large percentage boiling before reaching the other jaw. According to this embodiment, the gutters 39 can be fabricated from any material that is non-conducting, for example, plastic. The gutters can slide toward the distal end of the device as part of the activation of lever 21 shown in FIG. 7, to be stopped automatically by the presence of tissue. Alternatively the gutters 39 can be slid forward as part of a separate mechanism action. The gutters 39 can be fabricated from any suitable material that is non-conducting, for example, plastic.

Figure 14:
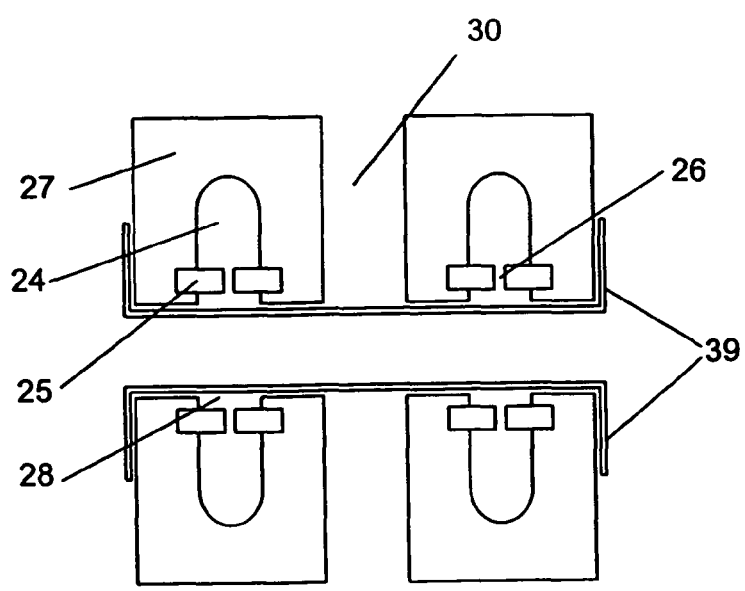
FIG. 14 is a schematic close-up cross-section view along line A-A of FIG. 9, showing the two gutters positioned to collect and direct saline flow distally.

FIG. 14 shows a schematic cross-sectional view of the gutters shown in FIG. 13. The cross-section in FIG. 14 illustrates the nonconducting portion 27 of the jaw 18, the saline manifold 24, the electrodes 25, holes 26, groove 28, space 30 for the cutting mechanism, and gutters 39. Near the distal end of the gutters, exit grooves 62 in the gutter can allow saline to flow through and onto the edge of the tissue even if the gutter is pressed snuggly against the tissue (shown in FIG. 8).

Figure 15:
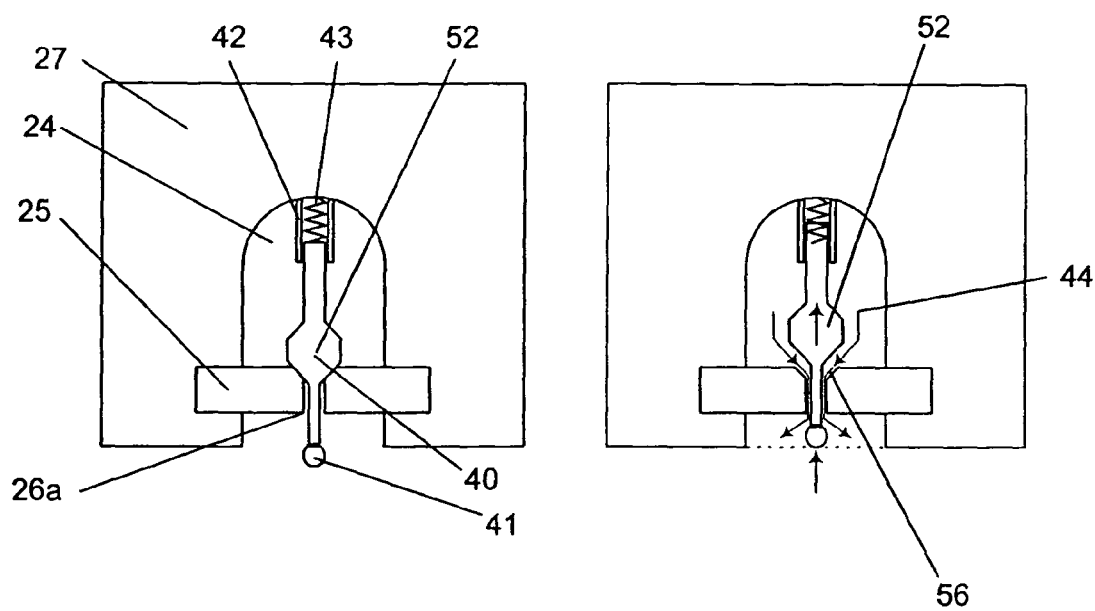
FIG. 15 is a schematic close-up cross-section view of one embodiment of the jaws of the device shown in FIG. 9, wherein the jaws include a tissue-activated valve.
Figure 16:
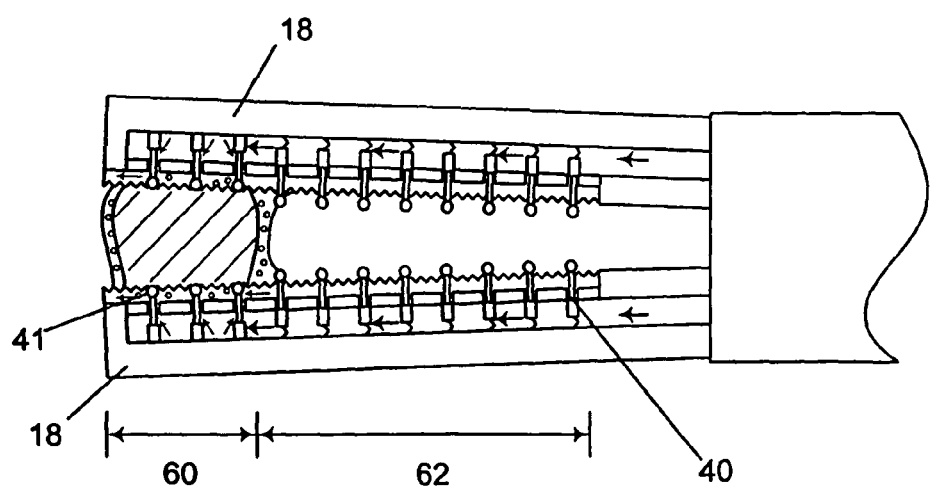
FIG. 16 is a schematic close-up side section view of one embodiment of the jaws of the device shown in FIG. 9, wherein the jaws include tissue-activated valves to direct flow distally.

FIG. 15 and FIG. 16 illustrate an alternative embodiment of the electrosurgical device of the invention. In this embodiment, the electrosurgical device includes a mechanism for directing saline flow to where tissue is being heated using RF energy. Preferably, the mechanism for directing saline flow comprises one or more tissue activated valves. In FIG. 15, the jaw 18 of the device includes a pin 40 that is configured with a bulged portion 52 in the middle section of the plunger pin 40, so that the pin 40 can seat into a counter-sunk hole 26a in the electrode 25. Pin 40 preferably further includes a pin tip 41 that contacts tissue. Preferably, the pin tip 41 is rounded or atraumatic to reduce tissue trauma As illustrated in the figure, counter-sunk hole 26a includes a recessed portion 56 that is configured to receive the bulged portion 52, such that when seated within the recessed portion 56, the pin 40 prevents conductive fluid flow from the manifold 24 to the tissue being treated. Preferably, a guide tube 42 holds the pin 40 in position, and spring 43 provides force to push the bulged portion 52 of pin 40 into the recessed portion 56 and seal off the flow of saline from the manifold region 24. In use, the pin tip 41 contacts tissue when the jaws 18 compress tissue. When tissue is compressed, the tissue contacts the tip 41 and pushes the pin 40 upwards, unseating the bulged portion 52 of the pin 40 from the recessed portion 56, and allowing saline to flow in direction of arrows 44 through the annular space between the pin 40 and the counter-sunk hole 26a.

FIG. 16 shows a schematic view of one embodiment wherein a series of such tissue-activated valves functions to deliver saline flow only to areas of the jaws where tissue is compressed and to be RF-heated. Referring to FIGS. 15 and 16, tissue is compressed in the area labeled 60, and the holes 26a are open to allow saline flow to the tissue treatment site. As described above, tissue contacts tip 41, thereby pushing pin 40 upwards, unseating the bulged portion 52 of the pin 40 from the recessed portion 56 (shown in FIG. 15). This interaction allows saline to flow from the device 5a to the tissue being treated. In the area labeled 62 in the figure, tissue is not compressed between jaws 18 of the device 5a, and therefore the holes 26a are closed to the flow of saline from the device 5a. Because the tips 41 of pins 40 do not contact tissue, the pin 40 is not forced from its seated position within recessed portion 56 of the hole 26a (shown in FIG. 15).

Generally, the holes 26 or 26a of the electrode 25 supply conductive fluid to the treatment site. In an alternative embodiment, these holes are provided in the form of porous material such as metal. In this embodiment, the electrodes do not include discrete holes; rather, the electrode surface itself is porous to allow infusion of the conductive solution to the treatment site. Porous sintered metal is available in many materials (such as, for example, 316L stainless steel, titanium, Ni-Chrome, and the like) and shapes (such as cylinders, discs, plugs, and the like) from companies such as Porvair, located in Henderson, N.C.

Porous metal components can be formed by a sintered metal powder process or by injection molding a two-part combination of metal and a material that can be burned off to form pores that connect (open cell) to each other. Such methods are known in the art. In this embodiment, conductive fluid will flow out of the electrode everywhere the pores are open. Preferably, the exterior (that is, the portions of the components that do not comprise the portion of the device involved in tissue treatment) of such porous metal electrode components can be covered with a material that fills the pores and prevents both the flow of saline and the passing of electrical energy. Alternatively, the device can include gutters to prevent the flow of saline in areas where it is desired to prevent saline flow.

In yet another embodiment, a porous polymer is used in place of the porous metal. Although the polymer is non-conductive, the conductive solution provided will conduct the RF energy across the porous polymer wall and to the tissue to be treated. Suitable materials include high temperature open cell silicone foam and porous polycarbonates, among others. Porous ceramics also fall into this category, since they could distribute conductive fluid flow, withstand high temperatures and be machinable or moldable for manufacturing purposes. Preferably, the material used transmits both fluid flow and electrical energy; thus, materials with properties between high-electrical conductivity metals and low electrical conductivity polymers are also contemplated, such as porous carbon-filled polymers. In these embodiments, conductive fluid flow is distributed along the length of the electrodes, where porous material is used to fabricate the electrodes. All or a portion of the electrodes can be porous according to the invention.

While the invention has been described in relation to a bipolar electrosurgical device, it will be readily apparent that other electrosurgical devices can be easily adapted to be used in connection with the invention. For example, the electrosurgical device 5 in FIG. 1 can, in another embodiment, be provided as a monopolar device. In this embodiment, one of the wires going to the bipolar device would instead go to a ground pad dispersive electrode located on the patient's back or other suitable anatomical location. Minimally, the electrosurgical device will be capable of delivering RF power and conductive solution to tissue. For example, the device can comprise a straight needle having an interior lumen for transmitting conductive solution to the tissue. Alternatively, the electrosurgical device can comprise other configurations such as loops, forceps, blades, and the like.

Other suitable electrosurgical devices that can be used in connection with the invention described herein include, but are not limited to, devices described in U.S. patent application Ser. No. 09/668,403 (filed 22 Sep. 2000), U.S. Pat. No. 5,897,553 (issued 27 Apr. 1999), U.S. Pat. No. 6,063,081 (issued 16 May 2000), and U.S. Pat. No. 6,096,037 (issued 1 Aug. 2000).

Moreover, it will be readily apparent that other means can be used to provide heat to the tissue, in addition to the radio frequency power described herein.

One or more of the features of the previously described system can be built into a custom RF generator. This embodiment can provide one or more advantages. For example, this type of system can save space and reduce overall complexity for the user. This system can also enable the manufacturer to increase the power delivered into low impedance loads, thereby further reducing the time to achieve the desired tissue effects. This changes the curve of FIG. 5, by eliminating or reducing the slope of the low impedance ramp of power versus impedance.

To effectively treat thick tissues, it can be advantageous to have the ability to pulse the RF power on and off. Under some circumstances, the temperature deep in tissue can rise quickly past the 100° C. desiccation point even though the electrode/tissue interface is boiling at 100° C. This manifests itself as "popping," as steam generated deep in the tissue boils too fast and erupts toward the surface. In one embodiment of the invention, a switch is provided on the control device or custom generator to allow the user to select a "pulse" mode of the RF power. Preferably, the RF power system in this embodiment is further controlled by software.

In some embodiments, it can be desirable to control the temperature of the conductive fluid before it is released from the electrosurgical device. In one embodiment, a heat exchanger is provided for the outgoing saline flow to either heat or chill the saline. Pre-heating the saline to a predetermined level below boiling reduces the transient warm-up time of the device as RF is initially turned on, thereby reducing the time to cause coagulation of tissue. Alternatively, pre-chilling the saline is useful when the surgeon desires to protect certain tissues at the electrode/tissue interface and treat only deeper tissue. One exemplary application of this embodiment is the treatment of varicose veins, where it is desirable to avoid thermal damage to the surface of the skin. At the same time, treatment is provided to shrink underlying blood vessels using thermal coagulation. The temperature of the conductive fluid prior to release from the surgical device can therefore be controlled, to provide the desired treatment effect.

In another embodiment, the flow rate controller is modified to provide for a saline flow rate that results in greater than 100% boiling at the tissue treatment site. For example, the selection switch 12 of the flow rate controller 11 (shown in FIG. 1) can include settings that correspond to 110%, 120% and greater percentages of boiling. These higher settings can be of value to a surgeon in such situations as when encountering thick tissue, wherein the thickness of the tissue can increase conduction away from the electrode jaws. Since the basic control strategy neglects heat conduction, setting for 100% boiling can result in 80% of 90% boiling, depending upon the amount of conduction. Given the teachings herein, the switch of the flow rate controller can accommodate any desirable flow rate settings, to achieve the desired saline boiling at the tissue treatment site.

Some embodiments of the invention can provide one or more advantages over current electrosurgical techniques and devices. For example, the invention preferably achieves the desired tissue effect (for example, coagulation, cutting, and the like) in a fast manner. In a preferred embodiment, by actively controlling the flow rate of saline, both in quantity (Q vs. P) and location (for example, using gutters to direct fluid distally to tissue, using holes to direct flow of fluid, or other similar methods) the electrosurgical device can create a hot non-desiccating electrode/tissue interface and thus a fast thermally induced tissue coagulation effect.

The invention can, in some embodiments, deliver fast treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

In another aspect, the invention preferably provides an electrosurgical device design that is capable of quickly and effectively sealing a wide variety of tissue segment sizes. The electrosurgical device provides a number of characteristics that improve the ability to treat a wide variety of tissue size and thickness. For example, a preferred embodiment provides the ability to control the saline flow towards a high percentage boiling, for example, 80-100%. This reduces shunting of the RF by boiling off saline before it could flow to the other electrode, or by boiling the saline as it is in the process of flowing to the other electrode. In another aspect, one preferred embodiment includes gutters in connection with the electrodes. In this embodiment, saline flow is directed toward the tissue treatment site, thereby providing all or substantially all of the conductive fluid to the treatment site. Thus, the tissue being treated is sufficiently "protected" from desiccation by utilizing the controlled conductive fluid boiling described herein. Preferably, the tissue-activated jaws offer another way to provide the conductive fluid in proximity to where the RF power is turned into heat.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the extent they are not inconsistent with the teachings herein.

What is claimed is:

1. An electrosurgical apparatus to provide controlled delivery of radio-frequency power and a fluid to an electrosurgical hand device to treat tissue, the apparatus comprising:

a radio-frequency generator to deliver the radio-frequency power, the radio-frequency power from the radio-frequency generator selectable at a radio-frequency power level;

a pump to deliver the fluid;

a primer to prime the hand device with the fluid;

a control system comprising an open loop control system with respect to the tissue, the open loop control system having a functional relationship relating a flow of the fluid to be delivered by the pump to the radio-frequency power level, the functional relationship to increase the flow of the fluid in response to an increase in the radio-frequency power level and to decrease the flow of the fluid in response to a decrease in the radio-frequency power level;

a selection switch which changes the functional relationship relating the flow of the fluid to be delivered by the pump to the radio-frequency power level; and wherein the functional relationship relating a flow of the fluid to be delivered by the pump to the radio-frequency power level resides in a storage medium of the apparatus for use by a microprocessor, the functional relationship in the form of a mathematical equation having a proportionality constant and the selection switch changes the functional relationship by changing the proportionality constant.

2. The apparatus of claim 1 wherein:
the pump comprises a peristaltic pump.

3. The apparatus of claim 1 wherein:
the primer comprises a switch located on the apparatus.

4. An electrosurgical apparatus to provide controlled delivery of radio-frequency power and a fluid to an electrosurgical hand device to treat tissue, the apparatus comprising:

a radio-frequency generator to deliver the radio-frequency power, the radio-frequency power from the radio-frequency generator selectable at a radio-frequency power level;

a pump to deliver the fluid;

a primer to prime the hand device with the fluid;

a control system comprising an open loop control system with respect to the tissue, the open loop control system having a functional relationship relating a flow of the fluid to be delivered by the pump to the radio-frequency power level over a range of radio-frequency power levels;

a selection switch which changes the functional relationship relating the flow of the fluid to be delivered by the pump to the radio-frequency power level over the range of radio-frequency power levels; and wherein the functional relationship relating a flow of the fluid to be delivered by the pump to the radio-frequency power level over a range of radio-frequency power levels resides in a storage medium of the apparatus for use by a microprocessor, the functional relationship in the form of a mathematical equation having a proportionality constant and the selection switch changes the functional relationship by changing the proportionality constant.

5. An electrosurgical apparatus to provide controlled delivery of radio-frequency power and a fluid to an electrosurgical hand device to treat tissue, the apparatus comprising:

a radio-frequency generator to deliver the radio-frequency power, the radio-frequency power from the radio-frequency generator selectable at a radio-frequency power level;

a pump to deliver the fluid;

a control system comprising a functional relationship relating a flow of the fluid to be delivered by the pump to the radio-frequency power level, the functional relationship to increase the flow of the fluid in response to an increase in the radio-frequency power level and to decrease the flow of the fluid in response to a decrease in the radio-frequency power level;

a selection switch which changes the flow of the fluid at the radio-frequency power level; and wherein the functional relationship relating a flow of the fluid to be delivered by the pump to the radio-frequency power level resides in a storage medium of the apparatus for use by a microprocessor, the functional relationship in the form of a mathematical equation having a proportionality constant and the selection switch changes the flow of the fluid at the radio-frequency power level by changing the proportionality constant.

6. The apparatus of claim 5 further comprising:
a primer to prime the hand device with the fluid.

7. The apparatus of claim 5 wherein:
the pump comprises a peristaltic pump.

* * * * *